(12) United States Patent
Licha et al.

(10) Patent No.: US 6,447,749 B1
(45) Date of Patent: Sep. 10, 2002

(54) PERFLUORO-ALKYL CONTAINING DYE MOLECULES AND GALENCIAL FORMULATIONS

(75) Inventors: Kai Licha, Falkensee (DE); Andreas Becker, Marktschwaben (DE); Bjoern Riefke, Madrid (ES); Johannes Platzek, Berlin (DE)

(73) Assignees: Schering Aktiengesellschaft, Berlin (DE); Institut fuer Diagnostikforschung, Berlin (DE)

( * ) Notice: Subject to any disclaimer, the term of this patent is extended or adjusted under 35 U.S.C. 154(b) by 0 days.

(21) Appl. No.: 09/672,051

(22) Filed: Sep. 29, 2000

Related U.S. Application Data

(60) Provisional application No. 60/158,306, filed on Oct. 8, 1999.

(30) Foreign Application Priority Data

Sep. 29, 1999 (DE) .......................... 199 48 650

(51) Int. Cl.$^7$ .................... A61K 49/00; A61K 49/04; A61B 10/00; C07D 207/06; C07D 295/02
(52) U.S. Cl. .................... 424/9.1; 424/9.6; 424/9.7; 424/9.42; 548/579
(58) Field of Search .................... 548/579; 424/1.65, 424/9.6, 9.5, 9.44, 9.42, 9.4, 9.1; 514/415

(56) References Cited

U.S. PATENT DOCUMENTS

| | | | | |
|---|---|---|---|---|
| 3,933,507 A | * | 1/1976 | von Konig et al. | 96/114.1 |
| 3,973,969 A | * | 8/1976 | Shiba et al. | 96/124 |
| 4,853,310 A | * | 8/1989 | Brown et al. | 430/83 |
| 5,254,455 A | * | 10/1993 | Hinz et al. | 430/584 |
| 5,277,895 A | * | 1/1994 | Platzek et al. | 424/9 |
| 5,281,593 A | * | 1/1994 | Gilmore et al. | 514/249 |
| 5,637,448 A | * | 6/1997 | Nakamura et al. | 430/588 |
| 5,690,909 A | * | 11/1997 | Platzek et al. | 424/9.363 |
| 5,851,752 A | * | 12/1998 | Uchida et al. | 430/572 |
| 5,980,864 A | * | 11/1999 | Platzek et al. | 424/9.363 |
| 5,986,086 A | * | 11/1999 | Brush et al. | 536/26.26 |
| 6,214,533 B1 | * | 4/2001 | Ho et al. | 430/584 |

FOREIGN PATENT DOCUMENTS

| | | | |
|---|---|---|---|
| GB | 686678 | * | 1/1953 |
| WO | 97261017 | * | 7/1997 |

* cited by examiner

*Primary Examiner*—Minna Moezie
*Assistant Examiner*—Lauren Q. Wells
(74) *Attorney, Agent, or Firm*—Millen, White, Zelano & Branigan, P.C.

(57) ABSTRACT

This invention describes galenical formulations that contain perfluoroalkyl-containing dye molecules and other perfluoroalkyl-containing substances. The new formulations are suitable as, i.a., contrast media for near-infrared diagnosis.

20 Claims, 7 Drawing Sheets

PERFLUORO-ALKYL CONTAINING DYE MOLECULES AND GALENCIAL FORMULATIONS

This application claims the benefit of the filing date of U.S. Provisional Application Serial No. 60/158,306 filed Oct. 8, 1999.

The invention relates to the field of galenical formulations, which are used in particular as contrast media for the visualization of lymph nodes. The invention relates to the subject that is characterized in the claims, namely new galenical formulations that contain perfluoroalkyl-containing dye molecules and other perfluoroalkyl-containing substances.

Malignant tumors metastasize heaped in regional lymph nodes, whereby several lymph node stations can also be involved. Thus, lymph node metastases are found in about 50–69% of all patients with malignant tumors (Elke, Lymphographie [Lymphography], in: Frommhold, Stender, Thurn (eds.), Radiologische Diagnostik in Klinik und Praxis [Radiological Diagnosis in Clinical Studies and Practice], Volume IV, Thieme Verlag Stuttgart, 7th Ed., 434–496, 1984). The diagnosis of a metastatic attack of lymph nodes is of great importance with respect to the therapy and prognosis of malignant diseases. With the modern imaging methods (CT, US, and MRT), lymphogenous metastasis sites of malignant tumors are detected only inadequately, since in most cases, only the size and the shape of the lymph node can be used as a diagnostic criterion. Thus, small metastases in non-enlarged lymph nodes (<2 cm) are not distinguished from lymph node hyperplasias without a malignant attack (Steinkamp et al., Sonographie und Kernspintomographie: Differentialdiagnostik von reaktiver Lymphknotenvergrböerung und Lymphknotenmetastasen am Hals [Sonography and Nuclear Spin Tomography: Differential Diagnosis of Reactive Lymph Node Enlargement and Lymph Node Metastases on the Neck], Radiol. Diagn. 33: 158, 1992).

It would be desirable to distinguish between lymph nodes with metastatic attack and hyperplastic lymph nodes with the aid of specific contrast media. In this case, the contrast medium could be adminisitered intravasally or interstitially/intracutaneously (see above Siefert, H. M. et al., Lymphology 13, 150–157, 1980). The interstitial/intracutaneous administration has the advantage that the substance is transported directly from the scattering focus (e.g., primary tumor) by the corresponding lymph tract into the potentially related regional lymph node stations. Likewise, a high concentration of the contrast medium in the lymph nodes can be achieved with a low dose. Such markers that are to be administered interstitially were mainly used in the nuclear-medicine evaluation (with use of radioactive particles, such as, e.g., $^{198}$Au-colloid). Nuclear-medicine methods have only a very inadequate spatial resolution, however, in contrast to nuclear spin tomography with its high spatial resolution in the range of fractions of a millimeter. The direct x-ray-lymphography (injection of an oily contrast medium suspension in a prepared lymph vessel) is an invasive method that is used very rarely and that can visualize only a few lymph outflow stations. Fluorescence-labeled dextrans are also used experimentally in animal experiments to be able to observe the lymph outflow after their interstitial administration. All commonly used markers for the visualization of lymph tracts and lymph nodes after interstitial/intracutaneous administration have in common the fact that they are substances with a particulate nature ("particulates," e.g., emulsions and nanocrystal suspensions) or large polymers (see above, WO 90/14846). The previously described preparations have proven to be of value, however, based on their inadequate local and systemic compatibility as well as their small lymph passageway, which produces an inadequate diagnostic efficiency, in most cases unsuitable for indirect lymphography.

There is generally a greet need, therefore, for lymph-specific contrast media with suitable pharmaceutical and pharmacological properties. In the pharmaceutical properties, focus is placed first on the highest possible contrast medium concentration and an adequate stability. In the case of the pharmacological properties, and in addition to a diagnostically relevant lymph concentration that is as uniform as possible over several (or in the case of intravenous administration over all) lymph stations, focus is placed mainly on a quick and complete excretion of the contrast medium to avoid an unnecessary load of the entire organism. Moreover, corresponding preparations must have at their disposal an adequate local and acute compatibility.

With respect to the application in radiological practice and in addition to as simple an application as possible of corresponding preparations, the quick "start-up" of the preparations is of central importance. Thus, if at all possible, it should be possible to perform imaging within a few hours after the administration of the contrast media.

Contrast media that are suitable for the visualization of lymph nodes in nuclear spin tomography are described in German Laid-Open Specification DE 196 03 033. There, perfluoroalkyl-containing metal complexes are disclosed, which are preferably used as lymphographic agents (see FIG. 1 of DE 196 03 033). Similar metal complexes that are suitable especially as blood-pool agents are described in German Laid-Open Specification DE 197 29 013.

A process for in-vivo diagnosis with use of NIR radiation is described in International Application WO 96/17628. Such diagnostic processes are at present under development. The contrast media that are described in this document are not suitable for visualizing the lymph nodes. There is therefore a need for suitable lymph-specific contrast media for these new diagnostic processes.

The object of this invention is therefore to make available new galenical formulations that are suitable as contrast media especially for the visualization of lymph nodes in the above-mentioned new diagnostic processes, and that meet the above-mentioned pharmaceutical and pharmacological requirements.

This object is achieved by the galenical formulations of this invention.

The new galenical formulations contain perfluoroalkyl-containing dye molecules, which can be used as contrast media in near-infrared diagnosis. The dyes satisfy certain photophysical and chemical requirements. They have high absorption coefficients and high fluorescence quantum yields to produce an effective signal even at the lowest tissue concentrations. The absorption maxima overlap a wide spectral range in a freely selectable manner. For detection in lower tissue layers (several centimeters under the surface), the spectral range between 600 and 900 nm is essential, while absorption wavelengths of 400 to 600 nm are sufficient for surface detection. The dyes further have a high chemical stability and photostability. When using light for fluorescence stimulation, the essential problem is the limited penetration depth of the light, which lies in the submillimeter range in the VIS but can be in the centimeter range in the NIR. With respect to the penetration depth, detection processes in surface tissue diseases, as well as soft tissues, are unproblematic. Since a considerable number of tissue changes (e.g., breast tumors, skin tumors, lymph node changes) are located on the surface, optical diagnostic processes in addition to the conventional methods are offered to perform a tissue differentiation based on different absorption and fluorescence patterns. In this case, the pronounced diffusion of light, which obtains increasing influence with growing tissue thickness, reduces both the resolution and the contrast of an optical image. Dyes that are used as so-called optical contrast media and are concentrated in the tissues that are to be detected can result in principle in an increase of the diagnostic value of optical detection processes, in which they increase the absorption of the tissue and provide an additional measurement signal with the dye-specific fluorescence, which can be detected arbitrarily often in front of a low tissue background with high sensitivity.

Preferred are dyes from the following classes:

Polymethine dyes, such as, e.g., cyanine dyes, squarilium dyes, croconium dyes, oxonol dyes, merocyanine dyes, cryptocyanine dyes;

xanthine dyes, such as, e.g., fluorescein and rhodamine and derivatives thereof;

heteroaromatic, cationic dyes, such as, e.g., oxazines, phenoxazines, thiazines, phenothiazines.

The new perfluoroalkyl-containing dye molecules are compounds of general formula I

(I)

in which $R_f$ represents a straight-chain or branched perfluoroalkyl radical with 4 to 30 carbon atoms, L stands for a linker, and A stands for a dye molecule.

Linker L is a direct bond or a straight-chain or branched carbon chain with up to 20 carbon atoms, which can be substituted with one or more —OH, —COO, —SO$_3$ groups and/or optionally is interrupted by one or more —O—, —S—, —CO—, —CONH—, —NHCO—, —CONR—, —NRCO—, —SO$_2$—, —NH—, —NR groups or a piperazine, whereby R stands for a $C_1$ to $C_{10}$ alkyl radical, which optionally is substituted with one or more OH groups and/or is interrupted by one or more oxygen atoms.

Dye molecule A is a dye from the class of the polymethine dyes, xanthine dyes or the heteroaromatic cationic dyes. Dye molecule A is preferably a cyanine dye, squarilium dye, croconium dye, oxonol dye, merocyanine dye, cryptocyanine dye, fluorescein dye, rhodamine dye, oxazine dye, phenoxazine dye, thiazine dye or phenothiazine dye. Especially preferably dye molecule A is a molecule according to general formula II:

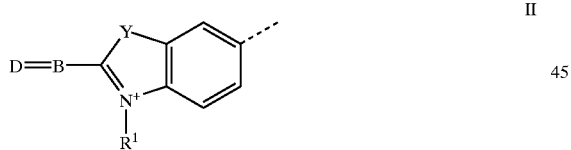

II in which

D stands for a fragment that corresponds to general formulas III to VI, whereby the position that is characterized with a star means the linkage with B:

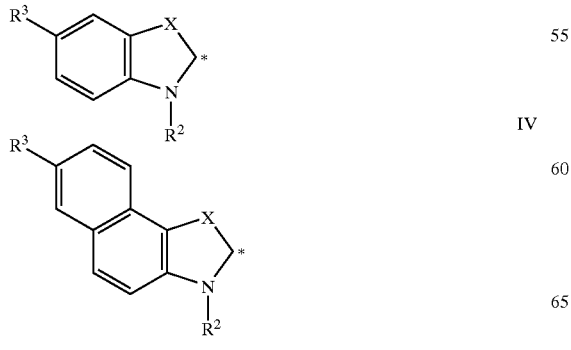

III

IV

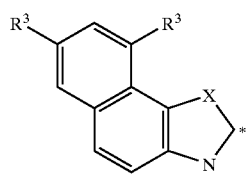

V

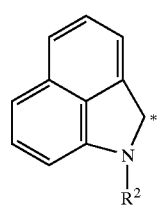

VI and in which B stands for a fragment that corresponds to general formulas VII to XII:

VII

VIII

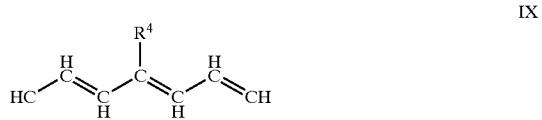

IX

X

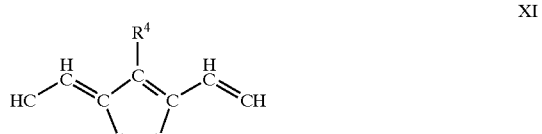

XI

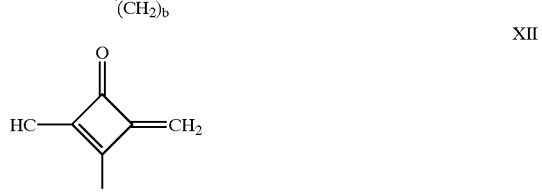

XII whereby $R^1$ and $R^2$ represent a $C_1$–$C_4$ sulfoalkyl chain, a saturated or unsaturated, branched or straight-chain $C_1$–$C_{50}$ alkyl chain, whereby the chain or parts of this chain optionally can form one or more aromatic or saturated, cyclic $C_5$–$C_6$ units or bicyclic $C_{10}$ units, and whereby the $C_1$–$C_{50}$ alkyl chain optionally is interrupted by 0 to 15 oxygen atoms and/or by 0 to 3 carbonyl groups and/or is substituted with 0 to 5 hydroxy groups, $R^3$ stands for a radical —COOE$^1$, —CONE$^1$E$^2$, —NHCOE$^1$, —NHCONHE$^1$, —NE$^1$E$^2$, —OE$^1$, —OSO$_3$E$^1$, —SO$_3$E$^1$, —SO$_2$NHE$^1$, —E$^1$, whereby $E^1$ and $E^2$, independently of one another, represent a hydrogen atom, a $C_1$–$C_4$ sulfoalkyl chain, a saturated or unsaturated, branched or straight-chain $C_1$–$C_{50}$ alkyl chain, whereby the chain or parts of this chain optionally can form one or more aromatic or saturated cyclic $C_5$–$C_6$ units or bicyclic $C_{10}$ units, and whereby the $C_1$–$C_{50}$ alkyl chain optionally is interrupted by 0 to 15 oxygen atoms and/or by 0 to 3 carbonyl groups, and/or is substituted with 0 to 5 hydroxy groups, and whereby $R^4$ stands for a hydrogen atom, a fluorine, chlorine, bromine or iodine atom, or a branched or straight-chain $C_1$–$C_{10}$ alkyl chain, b means a number 2 or 3, and X and Y, independently of one another, mean O, S, —CH═CH— or $C(CH_3)_2$.

Especially preferred perfluoroalkyl-containing dye molecules contain a perfluoroalkyl radical $R_f$ with 6 to 12 carbon atoms, a linker L, which consists of a $C_1$–$C_{10}$ alkyl group that contains one or more oxygen atoms and/or one or more —CONH—, —NHCO—, —CONR—, —NRCO groups, in which R stands for a $C_1$–$C_5$ alkyl radical, which can be substituted with one or more OH groups and a cyanine dye as a dye molecule. Among the cyanine dyes, indocarbocyanine dyes, indodicarbocyanine dyes and indotricarbocyanine dyes are preferred. Especially preferred dye molecules are the following compounds:

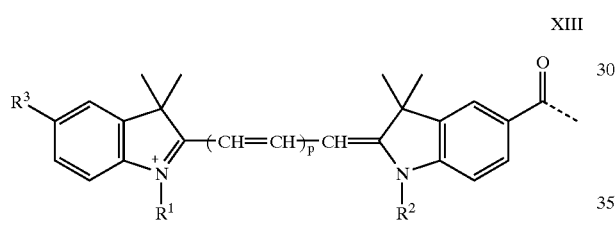

XIII in which p stands for 1, 2 or 3, $R^1$ and $R^2$, independently of one another, stand for a 4-sulfobutyl, 3-sulfopropyl, 2-sulfoethyl-, 3-methyl-3-sulfopropyl, methyl, ethyl or propyl radical, and $R^3$ stands for hydrogen, for a radical —$COOE^1$, —$CONE^1E^2$, —$NHCOE^1$, —$NHCONHE^1$, —$NE^1E^2$, —$OE^1$, —$OSO_3E^1$, —$SO_3$, $E^1$, —$SO_2NHE^1$, whereby $E^1$ and $E^2$, independently of one another, stand for a hydrogen atom or for a methyl, ethyl or a $C_3$–$C_6$ alkyl radical, which is interrupted by 0 to 2 oxygen atoms and/or by 0 to 1 carbonyl groups and/or is substituted with 0 to 5 hydroxy groups or stands for a poly(oxyethylene)glycol radical with 2 to 30 —$CH_2CH_2O$ units.

The galenical formulations according to the invention further contain other perfluoroalkyl-containing compounds, e.g., perfluoroalkyl-containing metal complexes. Perfluoroalkyl-containing metal complexes and their production were already described in the German Laid—Open Specifications DE 196 03 033, DE 197 29 013 and WO 97/26017. These perfluoroalkyl-containing metal complexes are compounds of general formula XIV $R_f$—M   (XIV)

in which $R_f$ represents a straight-chain or branched perfluoroalkyl radical with 4 to 30 carbon atoms, and M is a molecule portion that contains 1–6 metal complexes.

Molecule M stands for, for example, a group L—$M^1$, whereby L stands for a linker, and $M^1$ stands for a metal complex with an open-chain or cyclic chelator, which contains as central atom an atom of atomic numbers 21–29, 39, 42, 44 or 57–83. In this case, linker L is a direct bond, a methylene group, an —NHCO group, a group

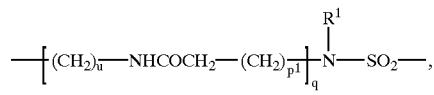

whereby $p^1$ means the numbers 0 to 10, q and U, independently of one another, mean the numbers 0 or 1, and $R^1$ means a hydrogen atom, a methyl group, a —$CH_2$—OH group, a —$CH_2$—$CO_2H$ group or a $C_2$–$C_{15}$ chain, which optionally is interrupted by 1 to 3 oxygen atoms, 1 to 2>CO groups or an optionally substituted aryl group and/or is substituted with 1 to 4 hydroxyl groups, 1 to 2 $C_1$–$C_4$ alkoxy groups, 1 to 2 carboxy groups, or a straight-chain, branched, saturated or unsaturated $C_2$–$C_{30}$ carbon chain, which optionally contains 1 to 10 oxygen atoms, 1 to 3 —$NR^1$ groups, 1 to 2 sulfur atoms, a piperazine, a —$CONR^1$ group, an —$NR^1CO$ group, an —$SO_2$ group, an —$NR^1$—$CO_2$ group, 1 to 2 CO groups, a group

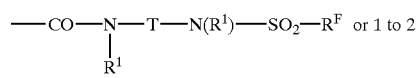

optionally substituted aryls and/or is interrupted by these groups and/or is optionally substituted with 1 to 3 —$OR^1$ groups, 1 to 2 oxo groups, 1 to 2 —NH—$COR^1$ groups, 1 to 2 —$CONHR^1$ groups, 1 to 2 (—$CH_2$)$_p$—$CO_2H$ groups, 1 to 2 groups —$(CH_2)_p$—$(O)_q$—$CH_2CH_2R^F$, whereby $R^1$, $R^F$ and p and q have the above-indicated meanings, and T means a $C_2$–$C_{10}$ chain, which optionally is interrupted by 1 to 2 oxygen atoms or 1 to 2 —NHCO groups.

In this case, metal complex M' stands for the following metal complexes:

a complex of general formula XV

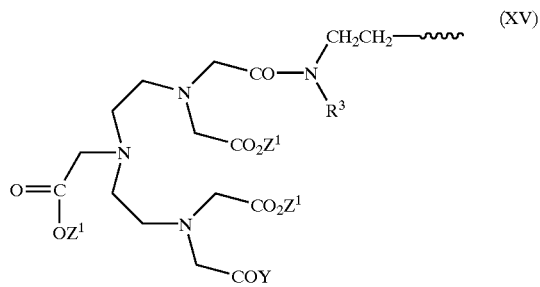

in which $R^3$, $Z^1$ and Y are independent of one another, and $R^3$ has the meaning of $R^1$ or —$(CH_2)_m$—L—$R^1$, whereby m is 0, 1 or 2, and L and $R^F$ have the above-mentioned meaning, $Z^1$, independently of one another, mean a hydrogen atom or a metal ion equivalent of atomic numbers 21–29, 39, 42, 44 or 57–83, Y means —OZ$^1$, or

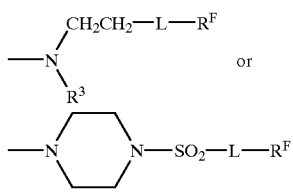

whereby Z$^1$, L, R$^F$ and R$^3$ have the above-mentioned meanings, a complex of general formula XVI

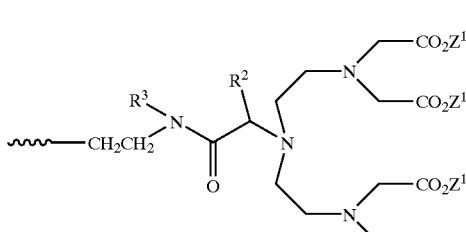
(XVI)

in which R$^3$ and Z$^1$ have the above-mentioned meanings, and R$^2$ has the meaning of R$^1$, a complex of general formula XVII

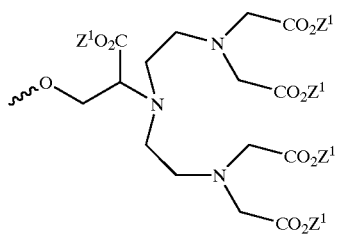
(XVII)

in which Z$^1$ has the above-mentioned meaning, a complex of general formula XVIII

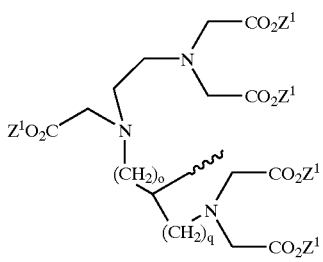
(XVIII)

in which Z$^1$ has the above-mentioned meaning, and o and q stand for numbers 0 or 1, and yields the sum o+q=1, a complex of general formula XIX

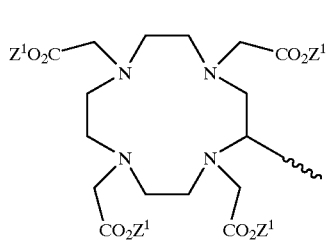
(XIX)

in which Z$^1$ has the above-mentioned meaning, a complex of general formula XX

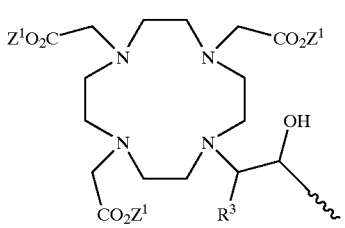
(XX)

in which Z$^1$ and Y have the above-mentioned meanings, a complex of general formula XXI

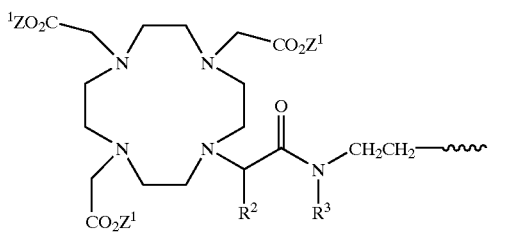
(XXI)

in which R$^3$ and Z$^1$ have the above-mentioned meanings, and R$^2$ has the above-mentioned meaning of R$^1$, a complex of general formula XXII (XXII)

in which R$^3$ and Z$^1$ have the above-mentioned meanings, a complex of general formula XXIII

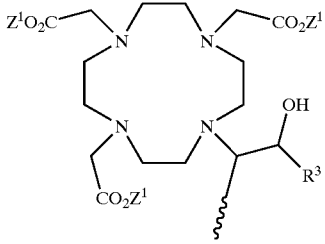

(XXIII)

in which $R^3$ and $Z^1$ have the above-mentioned meanings,
a complex of general formula XXIV

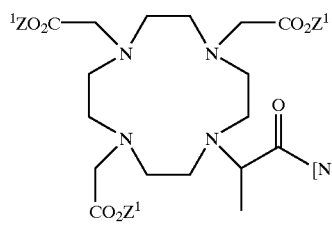

(XXIV)

in which $Z^1$, p and q have the above-mentioned meaning, and $R^2$ has the meaning of $R^1$, a complex of general formula XXV

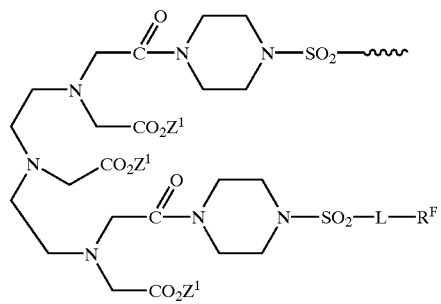

(XXV)

in which L, $R^F$ and $Z^1$ have the above-mentioned meanings, a complex of general formula XXVI

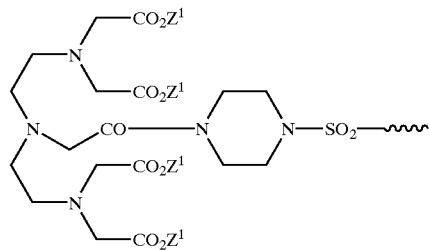

(XXVI)

in which $Z^1$ has the above-mentioned meaning.

Such compounds and production thereof are described in German Laid—Open Specification DE 196 03 033 A1 and in International Patent Application WO 97/26017.

Molecule portion M according to formula XIV can further exhibit the following structure:

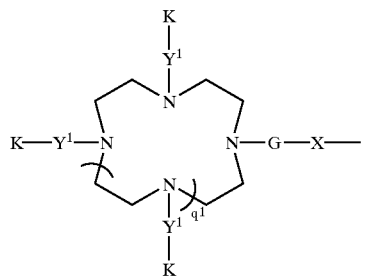

whereby
$q^1$ is a number 0, 1, 2 or 3,

K stands for a complexing agent or metal complex or salts thereof of organic and/or inorganic bases or amino acids or amino acid amides, X is a direct bond for the perfluoroalkyl group, a phenylene group or a $C_1$–$C_{10}$ alkyl chain, which optionally contains 1–15 oxygen atoms, 1–5 sulfur atoms, 1–10 carbonyl groups, 1–10 (NR) groups, 1–2 $NRSO_2$ groups, 1–10 CONR groups, 1 piperidine group, 1–3 $SO_2$ groups, 1–2 phenylene groups or optionally is substituted by 1–3 radicals $R^F$, in which R stands for a hydrogen atom, a phenyl, benzyl or a $C_1$–$C_{15}$ alkyl group, which optionally contains 1–2 NHCO groups, 1–2 CO groups, 1–5 oxygen atoms and optionally is substituted by 1–5 hydroxy, 1–5 methoxy, 1–3 carboxy, 1–3 $R^F$ radicals, $Y^1$ is a direct bond or a chain of general formula XXVII or XXVIII:

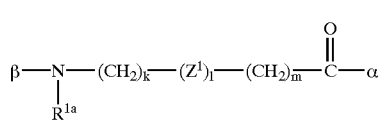

(XXVII)

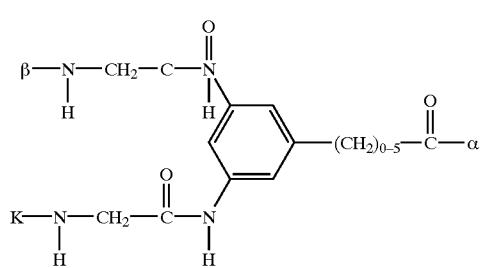

(XXVIII)

in which
$R^{1a}$ is a hydrogen atom, a phenyl group, a benzyl group or a $C_1$–$C_7$ alkyl group, which optionally is substituted with a carboxy group, a methoxy group or a hydroxy group, $Z^1$ is a direct bond, a polyglycol ether group with up to 5 glycol units or a molecule portion of general formula XXIX

 (XXIX)

in which $R^{2a}$ is a $C_1$–$C_7$ carboxylic acid, a phenyl group, a benzyl group or a —$(CH_2)_{1-5}$—NH—K group, α represents the binding to the nitrogen atom of the skeleton chain, β represents the binding to the complexing agent or metal complex K, and in which variables k and m stand for natural numbers between 0 and 10, and 1 stands for 0 or 1, and whereby G is a CO or $SO_2$ group.

Such compounds and the production thereof are described in German Laid Open Specification DE 197 29 013 A1.

Molecule portion A according to general formula I further can stand for a group $L^1$—$M^2$, in which $L^1$ stands for a linker and $M^2$ stands for a metal complex. In this case, linker $L^1$ is a molecule portion according to general formula XXX

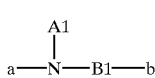 (XXX)

in which

N represents a nitrogen atom,

A1 means a hydrogen atom, a straight-chain or branched $C_1$–$C_{30}$ alkyl group, which optionally is interrupted by 1–15 oxygen atoms and/or optionally is substituted with 1–10 hydroxy groups, 1–2 COOH groups, a phenyl group, a benzyl group and/or 1–5 —$OR^4$ groups, with $R^4$ in the meaning of a hydrogen atom or a $C_1$–$C_7$ alkyl radical, or B1—$R^F$, B1 means a straight-chain or branched $C_1$–$C_{30}$ alkylene group that optionally is interrupted by 1–10 oxygen atoms, 1–5 —NH—CO groups, 1–5 —CO—NH groups, by a phenylene group (that is optionally substituted by a COOH group), 1–3 sulfur atoms, 1–2 —N(B2)—$SO_2$ groups, and/or 1–2 —$SO_2$—N(B2) groups with B2 in the meaning of A1, an NHCO group, a CONH group, an N(B2)—$SO_2$ group, or an —$SO_2$—N(B2) group and/or optionally is substituted with radical $R^F$, and in which a represents the binding to metal complex $M^2$, and b represents the binding to perfluoroalkyl group $R^F$.

In this case, metal complex $M^2$ stands for a metal complex of general formula XXXI

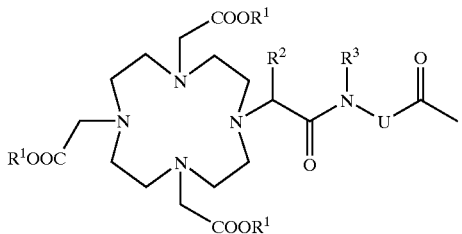 (XXXI)

whereby $R^1$ stands for a hydrogen atom or a metal ion equivalent of atomic numbers 21–29, 31, 32, 37–39, 42–44, 49 or 57–83, $R^2$ and $R^3$ stand for a hydrogen atom, a $C_1$–$C_7$ alkyl group, a benzyl group, a phenyl group, —$CH_2OH$ or —$CH_2$—$OCH_3$, U stands for radical L, whereby L and U, independently of one another, can be the same or different, however.

Such compounds and their production are described in the German patent application with file number 199 14 101.0 as well as in the examples below.

Especially preferred are metal complexes in which the central atom is a gadolinium atom (atomic number 64). Metal complexes with cyclic chelating agents are preferred compared to those with open-chain chelating agents.

Especially preferred gadolinium complexes are the gadolinium complex of 10-[1-methyl-2-oxo-3-aza-5-oxo-5-{4-perfluorooctylsulfonyl-piperazin-1-yl}-pentyl]-1,4,7-tris (carboxymethyl)-1,4,7,10-tetraazacyclododecane (for production, see WO 97/26017, Example 33), the gadolinium complex of 10-[2-hydroxy-4-aza-5-oxo-7-oxa-10,10,11,11,12,12,13,13,14,14,15,15,16,16,17,17,17-heptadecafluoroheptadecyl]-1,4,7-tris (carboxymethyl)-1,4,7,10-tetraazacyclododecane (for production, see DE 196 03 033, Example 2), 1,4,7-tris{1,4,7-tris(N-carboxylatomethyl)-10-(N-1-methyl-3,6-diaza-2,5,8-trioxooctane-1,8-diyl)-1,4,7,10-tetraazacyclododecane, Gd-complex}-10-(N-2H,2H,4H,4H,5H,5H-3-oxa-perfluoro-tridecanoyl)-1,4,7,10-tetraazacyclododecane (for production, see DE 197 29 013, Example 1), 1,4,7-tris{1,4,7-tris[(N-carboxylatomethyl)]-10-[N-1-methyl-3-aza-2,5-dioxopentam-1,5-diyl]-1,4,7,10-tetraazacyclododecane, Gd complex}-10-[2-(N-ethyl-N-perfluorooctylsulfonyl)-amino]-acetyl-1,4,7,10-tetraazacyclododecane (for production, see DE 197 29 013, Example 12), the gadolinium complex of 10-[2-hydroxy-4-aza-5-oxo-7-aza-7(perfluorooctylsulfonyl)-nonyl]-1,4,7-tris (carboxymethyl)-1,4,7,10-tetraazacyclododecane (for production, see DE 196 03 033, Example 1), 1,4,7-tris(carboxylatomethyl)-10-[(3-aza-4-oxo-hexan-5-ylic)-acid-N-(2,3-dihydroxy-propyl)-N-(1H,1H,2H,2H,4H,4H,5H,5H-3-oxa)-perfluorotridecyl)-amide}-1,4,7,10-tetraazacyclododecane, gadolinium complex (for production see examples), 1,4,7-tris(carboxylatomethyl)-10-[(3-aza-4-oxo-hexan-5-ylic)-acid-N-(1H,1H,2H,2H,4H,4H,5H,5H-3-oxa-perfluorotridecyl)-amide]-1,4,7,10-tetraazacyclododecane, gadolinium complex (for production see examples), 1,4,7-tris(carboxylatomethyl)-10-{(3-aza-4-oxo-hexan-5-ylic)-acid-[N-3,6,9,12,15-pentaoxa)-hexadexyl)-N-(1H,1H,2H,2H,4H,4H,5H,5H-3-oxa)-perfluorotridecyl]-amide]-1,4,7,10-tetraazacyclododecane, gadolinium complex (for production, see examples), and 1,4,7-tris(carboxylatomethyl)-10-[(3-aza-4-oxo-hexan-5-ylic)-acid-N-(5-hydroxy-3-oxa-pentyl)-N-(1H,1H,2H,2H,4H,4H,5H,5H-3-oxa)-perfluorotridecyl)-amide]-1,4,7,10-tetraazacyclododecane, gadolinium complex (for production, see examples).

Instead of the perfluoroalkyl-containing metal complexes, other perfluoroalkyl-containing compounds can also be contained in the galenical formulations according to the invention. Such compounds are compounds of general formula XXXII $R_f$—$L^2$—$G^1$ (XXXII)

in which $R_f$ represents a straight-chain or branched perfluoroalkyl radical with 4 to 30 carbon atoms, $L^2$ stands for a linker, and $G^1$ stands for a hydrophilic group.

Linker $L^2$ is a direct bond, an —$SO_2$ group or a straight-chain or branched carbon chain with up to 20 carbon atoms, which can be substituted with one or more —OH, —COO, —$SO_{13}$ groups and/or optionally contains one or more —O—, —S—, —CO—, —CONH—, —NHCO—, —CONR"—, —NR"CO—, —$SO_2$—, —$PO_4$—, —NH—, —NR" groups, an aryl ring or a piperazine, whereby R" stands for a $C_1$ to $C_{20}$ alkyl radical, which in turn can contain one or more O-atoms and/or can be substituted with —COO— or $SO_3$ groups. Hydrophilic group $G^1$ stands for a monosaccharide or disaccharide, one or more adjacent —COO⁻ or —$SO_3$ groups, a dicarboxylic acid, an isophthalic acid, a picolinic acid, a benzenesulfonic acid, a tetrahydropyrane dicarboxylic acid, a 2,6-pyridinedicarboxylic acid, a quaternary ammonium ion, an aminopolycarboxylic acid, an aminodipolyethyleneglycolsulfonic acid, an aminopolyethylene glycol group, an $SO_2$—$(CH_2)_2$—OH group, a polyhydroxyalkyl chain with at least two hydroxyl groups or one or more polyethylene glycol chains with at least two glycol units, whereby the polyethylene glycol chains are terminated by an —OH or —$OCH_3$ group. Such substances are already known (see, e.g., Tetrahedron Letters, Vol. 36, No. 4, pp. 539–542, 1995). The synthesis of some of these compounds is described in detail in the examples below. Those compounds that contain a monosaccharide as hydrophilic group $G^1$ are preferably used.

Especially preferred perfluoroalkyl-containing compounds contain a perfluoroalkyl radical $R_f$ with 6 to 12 carbon atoms, a linker $L_2$, which represents an —$SO_2$ group or a straight-chain or branched carbon chain with up to 20 carbon atoms, which in turn contains one or more —O—, —CO—, —CONH—, —NHCO—, —CONR"—, NR"CO—, —$SO_2$ groups or a piperazine, in which R" has the above-indicated meaning, and a monosaccharide as hydrophilic group $G^1$.

It is also possible to produce galenical formulations with three components and to use the latter as contrast media for the visualization of lymph nodes. Such formulations are described in detail in the examples below.

The substance mixtures according to the invention can be present in dissolved form in a solvent. The solvent is preferably water. The proportion of the perfluoroalkyl-containing dye molecule is between 0.1 and 10 mol % relative to the total amount of perfluoroalkyl-containing substances, preferably between 1 and 10 mol %. Preferred are mixtures that consist of perfluoroalkyl-containing dye molecules and other perfluroalkyl-containing compounds, in which the perfluoroalkyl chains have a length of 6 to 12 carbon atoms. Especially preferred are mixtures in which both the perfluoroalkyl-containing dye molecules and the other perfluoroalkyl-containing compounds have a perfluoroalkyl chain with 8 carbon atoms.

The new galenical formulations show surprising advantages in their use as contrast media. Galenical formulations that consist of perfluoroalkyl-containing dye molecules and other perfluoroalkyl-containing substances can be produced in a wide variety. These formulations are suitable for fluorescence detection and visually detectable staining of lymph nodes after interstitial or intravenous administration.

Compared to the already known contrast media for visualization of the lymph nodes, they show an improved compatibility and an almost complete excretion. The local compatibility further is also higher than in the previously known contrast media, and the new formulations simultaneously show a higher organ specificity. The concentration in the lymph nodes is higher than in the known contrast media for lymphography. If perfluoroalkyl-containing dye molecules and perfluorine-containing metal complexes are used simultaneously, it is possible to use various diagnostic processes in succession. In addition to the near-infrared diagnosis, e.g., computer or nuclear spin tomography can also be performed.

Another advantage consists in the fact that the lymph nodes assume a characteristic coloring. In addition to the NIR diagnosis, this allows an intraoperative fluorescence diagnosis of the lymph node morphology and lymph tract permeability as well as a fluorescence-supported removal of biopsies. In this case, the fluorescence-supported detection of the so-called sentinel lymph node is especially important. The sentinel lymph node is the first lymph node that drains the lymphs of a tumor area and thus also the first lymph node that is affected in a metastasis attack of lymph nodes.

The fluorescence-supported detection of these lymph nodes is carried out very much more simply than, e.g., the detection with the aid of radiopharmaceutical agents, since the detection of x-ray radiation is always more difficult than direct detection of fluorescence radiation. In addition, the stained lymph nodes are to be made visible, since the lymph nodes also can assume a characteristic coloring in the case of the corresponding dosage of the compounds according to the invention.

The dye molecules are produced in a way that is similar to methods that are known in the literature and then coupled with perfluoroalkyl derivatives. Preferred are dyes from the above-mentioned classes, which contain carboxyl groups or isothiocyanate groups. Especially preferred are those dyes that contain carboxyl groups, which after activation with use of standard reagents are reacted with amino groups that contain perfluoroalkyl derivatives with the formation of an amide group. Literature for synthesis of polymethine dyes: Bioconjugate Chem. 4, 105–111, 1993; Bioconjugate Chem. 7, 356–62, 1996; Bioconjugate Chem. 8, 751–56, 1997; Cytometry 10, 11–19, 1989 and 11, 418–30, 1990; J. Heterocycl. Chem. 33, 1871–6, 1996; J. Org. Chem. 60, 2391–5, 1995; Dyes and Pigments 17, 19–27, 1991, Dyes and Pigments 21, 227–34, 1993; J. Fluoresc. 3, 153–155, 1993; Anal. Biochem. 217, 197–204, 1994; U.S. Pat. No. 4,981,977; U.S. Pat. No. 5,688,966; U.S. Pat. No. 5,808,044; WO 97/42976; WO 97/42978; WO 98/22146; WO 98/26077; EP 0800831.

The production of the galenical formulations is carried out in that the perfluoroalkyl-containing dye molecule (component A) and the other perfluoroalkyl-containing substance (component B) are weighed and are dissolved in a suitable solvent. An especially suitable solvent is water. As already mentioned above, the proportion of the perfluoroalkyl-containing dye molecule is between 1 and 10 mol % relative to the total amount of perfluoroalkyl-containing substances. The concentration of the solution is preferably between 0.1 mmol/L and 20 mmol/L relative to the dye. This solution is then added in excess to commonly used galenical additives, such as, e.g., buffer solutions and the Ca-salt of the complexing agent. At 10 to 100° C., the solutions are stirred vigorously. As an alternative, the solutions can be treated at 10 to 100° C. in an ultrasound bath. Another alternative consists in that the solutions are treated with microwaves.

In substances that do not dissolve in water as individual components, it has proven advantageous to add a solubilizer, such as alcohol (e.g., methanol or ethanol) or another water-miscible solvent and then to distill off the latter slowly. The distillation can take place under vacuum. The residue is then dissolved in water, and the solution is filtered.

It is also possible to dissolve each component per se separately in a solvent, then to join them and to proceed further as above.

Such produced solutions can be freeze-dried. The freeze-dried solutions can be dissolved again in water and retain, surprisingly enough, their advantageous properties. This allows a long storage time of the active ingredient.

With use as a contrast medium for the visualization of the lymph nodes, the aqueous solutions of the perfluoroalkyl-containing substances (at a concentration of between 0.1 mmol/L and 20 mmol/L relative to the dye, see above) are administered by interstitial/intracutaneous injection or intravenous injection at one or more injection sites. The administration volume relates to the species and form of administration between 0.1 ml and 30 ml, and the administered dose is preferably between 0.1 µmol/kg and 10 µmol/kg of body weight, relative to the dye.

After the galenic formulation is injected, light from the corresponding spectral range is irradiated for electronic stimulation of the dye that is used in the tissue. The reflected stimulation light or the fluorescence radiation that is emitted by the dye is recorded. Preferred are the methods in which the tissue irradiates over a large surface and the fluorescence radiation is triggered locally by recording with a CCD camera or the tissue areas that are to be formed are rastered with a fiber optic light guide, and the signals that are obtained are assembled by computer into a synthetic image. In this case, fluorescence can be detected and evaluated spectrally and/or by phase selection, as well as in a steady-state manner and/or in a time-resolved manner. The fluorescence images that are obtained can be produced at the same time as the white light images and are depicted above one another in a figure for data evaluation. In the case of intraoperative diagnosis, the staining can be observed visually in addition for fluorescence detection.

Figure 1A:
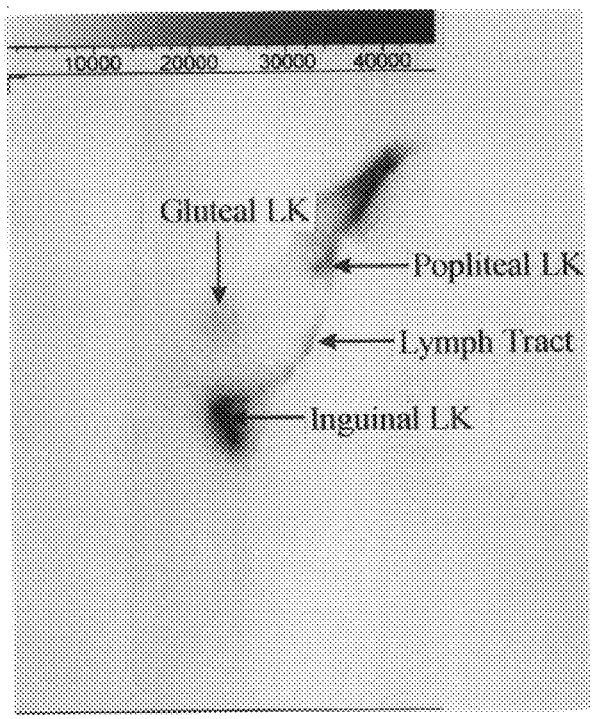
FIG. 1 shows near-infrared fluorescence images of a guinea pig (1a) abdominal view, and (1b) right lateral view, after interstitial/intracutaneous administration of a formulation, see Example 18.

The following examples explain the invention, without intending that it be limited to these examples.

EXAMPLES 1 AND 2

Synthesis of bis-Sulfobutyl-indocyanine Dyes 1,1'-bis-(4-Sulfobutyl)-indodicarbocyanine-5-Carboxylic Acid, Sodium Salt (1) and 1,1'-bis-(4-Sulfobutyl) indotricarbocyanine-5-carboxylic Acid, Sodium Salt (2) for Coupling to Perfluoroalkylamino Derivatives Synthesis is generally carried out starting from 1-(4-sulfobutyl)-2,3,3-trimethyl-3H-indolenine and 1-(4-sulfobutyl)-2,3,3-trimethyl-5-carboxy-3H-indolenine (Cytometry 10, 11–19, 1989, Talanta 39, 505–510, 1992)

EXAMPLE 1

Synthesis of 1,1'-bis-(4-Sulfobutyl) indodicarbocyanine-5-carboxylic Acid. Sodium Salt (1)

1.2 g (4.1 mmol) of 1-(4-sulfobutyl)-2,3,3-trimethyl-3H-indolenine and 1.0 g (3.9 mmol) of malonaldehyde-bis-phenylimine-hydrochloride are stirred into 15 ml of acetic acid anhydride for 30 minutes at 120° C. and then cooled to room temperature with a water bath. Then, 1.4 g (4.2 mmol) of 1-(4-sulfobutyl)-2,3,3-trimethyl-5-carboxy-3H-indolenine, 1.2 g (14.6 mmol) of anhydrous sodium acetate, 15 ml of acetic acid anhydride and 6 ml of acetic acid are added in succession. The reaction mixture is heated for 1 hour to 120° C., the reaction solution is cooled and mixed with 100 ml of ether. The precipitated solid is filtered off. Chromatographic purification is carried out on RP-silica gel EUROPREP 60-30 C18 (Knauer), 60A, 20–45 g (eluant: water/MeOH, step gradient of 0% to 70% MeOH). Methanol is removed from the product-containing fractions in a rotary evaporator, and the fractions are then freeze-dried, yield: 1.8 g (66%), blue lyophilizate.

EXAMPLE 2

Synthesis of 1,1'-bis-(4-Sulfobutyl) indotricarbocyanine-5-carboxylic Acid, Sodium Salt (2)

1.2 g (4.1 mmol) of 1-(4-sulfobutyl)-2,3,3-trimethyl-3H-indolenine and 1.1 g (3.9 mmol) of glutaconaldehyde-dianilhydrochloride are stirred in 15 ml of acetic acid anhydride for 30 minutes at 120° C. and then cooled to room temperature with a water bath. Then, 1.4 g (4.2 mmol) of 1-(4-sulfobutyl)-2,3,3-trimethyl-5-carboxy-3H-indolenine, 1.2 g (14.6 mmol) of anhydrous sodium acetate, 15 ml of acetic acid anhydride and 6 ml of acetic acid are added. The reaction mixture is heated for 1 hour to 120° C., the now blue solution is cooled and mixed with 100 ml of ether. The working-up and purification are carried out as described in Example 1, yield: 1.8 g (60%) of blue lyophilizate.

EXAMPLES 3 AND 4

Synthesis of Mono-sulfobutyl-indocyanine Dyes 1-Methyl-1'-(4-sulfobutyl)indodicarbocyanine-5-carboxylic Acid(3) and 1-Methyl-1'-(4-sulfobutyl) indotricarbocyanine-5-carboxylic Acid (4) for Coupling to Perfluoroalkylamino Derivatives The synthesis is generally carried out starting from 1-(4-sulfobutyl)-2,3,3-trimethyl-3H-indolenine and 1,2,3,3-tetramethyl-5-carboxy-3H-indolium iodide (Cytometry 10, 11–19, 1989, Talanta 39, 505–510, 1992).

EXAMPLE 3

Synthesis of 1-Methyl-1'-(4-sulfobutyl) indodicarbocyanine-5-carboxylic Acid (3)

1.2 g (4.1 mmol) of 1-(4-sulfobutyl)-2,3,3-trimethyl-3H-indolenine and 1.0 g (3.9 mmol) of malonaldehyde-bis-phenylimine-hydrochloride are stirred into 15 ml of acetic acid anhydride for 30 minutes at 120° C. and then cooled to room temperature with a water bath. Then, 1.6 g (4.6 mmol) of 1,2,3,3-tetramethyl-5-carboxy-3H-indolium iodide, 1.2 g (14.6 mmol) of anhydrous sodium acetate, 15 ml of acetic acid anhydride and 6 ml of acetic acid are added in succession. The reaction mixture is heated for 1 hour to 120° C., the now blue solution is cooled and mixed with 100 ml of ether. The precipitated solid is filtered off. A chromatographic purification of RP-silica gel EUROPREP 60–30 C18 (Knauer), 60A, 20–45µ is carried out (eluant: water/MeOH, step gradient of 30% to 90% MeOH). Methanol is removed from the product-containing fractions in a rotary evaporator and then freeze-dried, yield: 0.9 g (42%), blue lyophilizate.

EXAMPLE 4

Synthesis of 1-Methyl-1'-(4-sulfobutyl) indotricarbocyanine-5-carboxylic Acid (4)

1.2 g (4.1 mmol) of 1-(4-sulfobutyl)-2,3,3-trimethyl-3H-indolenine and 1.1 g (3.9 mmol) of glutaconaldehyde-dianilhydrochloride are stirred in 15 ml of acetic acid anhydride for 30 minutes at 120° C. and then cooled to room temperature with a water bath. Then, 1.6 g (4.6 mmol) of 1,2,3,3-tetramethyl-5-carboxy-3H-indolium iodide, 1.2 g (14.6 mmol) of anhydrous sodium acetate, 15 ml of acetic acid anhydride and 6 ml of acetic acid are added. The reaction mixture is heated for 1 hour to 120° C., the reaction solution is cooled and mixed with 100 ml of ether. The working-up and purification are carried out as described in Example 3. Yield: 1.4 g (62%) of blue lyophilizate.

EXAMPLES 5 TO 8

Synthesis of Perfluoroalkylated bis-sulfobutyl-cayanine Dyes 7 to 10

The synthesis is carried out from 1 to 2 by activation of carboxylic acid and reaction with 1H,1H,2H,2H,4H,4H,5H,5H-3-oxa-perfluorotridecylamine (5) to 7 and 8, and by reaction with N-(2,3-dihydroxypropyl)-N-(1H,1H,2H,2H,4H,4H,5H,5H-3-oxa-perfluorotridecyl)-amine (6) to 9 and 10. The synthesis of 5 and is described in DE 199 14 101.

0° C. with 0.5 mmol of TBTU in 10 ml of dimethylformamide and stirred for 15 minutes at 0° C. Then, a solution of 0.29 g (0.55 mmol) of 5 and 0.6 mmol of triethylamine in 5 ml of dimethylformamide is added in drops, and the reaction mixture is stirred for 2 hours at room temperature. After 50 ml of hexane/50 ml of ethyl acetate is added, the precipitated solid is filtered off and chromatographically purified on RP-silica gel Lichroprep$^{(R)}$ RP-8 (Merck), 40–63µ (eluant: water/MeOH, step gradient of 20% to 80% MeOH); yields: 0.42 g (71%) of 7, 0.45 g (75%) of 8.

EXAMPLES 7 AND 8

Synthesis of 9 and 10 From Dyes 1 and 2

A solution of 0.5 mmol of dye 1 or 2 and 0.1 g (1.0 mmol) of triethylamine in 20 ml of dimethylformamide is mixed at 0° C. with 0.5 mmol of TBTU in 10 ml of dimethylformamide and stirred for 15 minutes at 0° C. Then, a solution of 0.37 g (0.65 mmol) of 6 in 5 ml of dimethylformamide is added in drops, and the reaction mixture is stirred for 18 hours at room temperature. After 50 ml of hexane/50 ml of ethyl acetate is added, the precipitated solid is filtered off and purified chromatographically on RP-silica gel LiChroprep$^{(R)}$ RP-8 (Merck), 40–63µ (eluant: water/MeOH, step gradient of 20% to 80% MeOH); yields: 0.40 g (63%) of 9, 0.43 g (67%) of 10.

EXAMPLES 9 TO 12

Synthesis of Perfluoroalkylated Mono-sulfobutyl-cyanine Dyes 11 to 14

The synthesis that is embodied in the example is carried out from 3 or 4 by activation of the carboxylic acid and reaction with 1H,1H,2H,2H,4H,4H,5H,5H-3-oxa-perfluorotridecylamine (5) to 11 and 12, and by reaction with N-(2,3-dihydroxypropyl)-N-(1H,1H,2H,2H,4H,4H,5H,5H-3-oxa-perfluorotridecyl)-amine (6) to 13 and 14.

| # | M (g/mol) | |
|---|---|---|
| 7 | 1182.0 | 5-{N-[2-(3,3,4,4,5,5,6,6,7,7,8,8,9,9,10,10,10-heptadecafluorodecyloxy)ethyl]-aminocarbonyl}-2-{7-[1,3-dihydro-3,3-dimethyl-1-(4-sulfobutyl)-2H-indol-2-ylidene]-1,3-pentadienyl}-3,3-dimethyl-1-(4-sulfobutyl)-3H-indolium, internal salt, sodium salt |
| 8 | 1208.0 | 5-{N-[2-(3,3,4,4,5,5,6,6,7,7,8,8,9,9,10,10,10-heptadecafluoro-decyloxy)ethyl]-aminocarbonyl}-2-{7-[1,3-dihydro-3,3-dimethyl-1-(4-sulfobutyl)-2H-indol-2-ylidene]-1,3,5-heptatrienyl}-3,3-dimethyl-1-(4-sulfobutyl)-3H-indolium, internal salt, sodium salt |
| 9 | 1256.1 | 5-{N-[2-(3,3,4,4,5,5,6,6,7,7,8,8,9,9,10,10,10-heptadecafluorodecyloxy)ethyl]-N-(2,3-dihydroxypropyl)aminocarbonyl}-2-{7-[1,3-dihydro-3,3-dimethyl-1-(4-sulfobutyl)-2H-indol-2-ylidene]-1,3-pentadienyl}-3,3-dimethyl-1-(4-sulfobutyl)-3H-indolium, internal salt, sodium salt |
| 10 | 1282.1 | 5-{N-[2-(3,3,4,4,5,5,6,6,7,7,8,8,9,9,10,10,10-heptadecafluorodecyloxy)ethyl]-N-(2,3-dihydroxypropyl)aminocarbonyl}-2-{7-[1,3-dihydro-3,3-dimethyl-1-(4-sulfobutyl)-2H-indol-2-ylidene]-1,3,5-heptatrienyl}-3,3-dimethyl-1-(4-sulfobutyl)-3H-indolium, internal salt, sodium salt |

| # | M (g/mol) | |
|---|---|---|
| 11 | 1037.9 | 2-[5-(1-Ethyl)-1,3-dihydro-3,3-dimethyl-2H-indol-2-ylidene)-1,3-pentatrienyl]-5-{N-[2-(3,3,4,4,5,5,6,6,7,7,8,8,9,9,10,10,10-heptadecafluorodecyloxy)ethyl]-aminocarbonyl}-3,3-dimethyl-1-(4-sulfobutyl)-3H-indolium, internal salt, sodium salt |
| 12 | 1063.9 | 2-[5-(1-ethyl)-1,3-dihydro-3,3-dimethyl-2H-indol-2-ylidene)-1,3,5-heptatrienyl]-5-{N-[2-(3,3,4,4,5,5,6,6,7,7,8,8,9,9,10,10,10-heptadecafluorodecyloxy)-ethyl]-aminocarbonyl}-3,3-dimethyl-1-(4-sulfobutyl)-3H-indolium, internal salt, sodium salt |
| 13 | 1112.9 | 2-[5-(1-ethyl)-1,3-dihydro-3,3-dimethyl-2H-indol-2-ylidene)-1,3-pentatrienyl]-5-{N-[2-(3,3,4,4,5,5,6,6,7,7,8,8,9,9,10,10,10-heptadecafluorodecyloxy)ethyl]-N-(2,3-dihydroxypropyl)aminocarbonyl}-3,3-dimethyl-1-(4-sulfobutyl)-3H-indolium, internal salt, sodium salt |
| 14 | 1138.9 | 2-[5-(1-ethyl)-1,3-dihydro-3,3-dimethyl-2H-indol-2-ylidene)-1,3,5-heptatrienyl]-5-{N-[2-(3,3,4,4,5,5,6,6,7,7,8,8,9,9,10,10,10-heptadecafluorodecyloxy)-ethyl]-N-(2,3-dihydroxypropyl)aminocarbonyl}-3,3-dimethyl-1-(4-sulfobutyl)-3H-indolium, internal salt, sodium salt |

EXAMPLES 5 AND 6

Synthesis of 7 and 8 From Dyes 1 and 2

A solution of 0.5 mmol of dye 1 or 2 and 0.1 g (1.0 mmol) of triethylamine in 20 ml of dimethylformamide is mixed at

EXAMPLES 9 AND 10

Synthesis of 11 and 12 From Dyes 3 and 4

A solution of 0.5 mmol of dye 3 or 4 and 0.1 g (1.0 mmol) of triethylamine in 20 ml of dimethylformamide is mixed at 0° C. with 0.5 mmol of TBTU in 10 ml of dimethylformamide and stirred for 15 minutes at 0° C. Then, a solution of 0.29 g (0.55 mmol) of 5 and 0.6 mmol of triethylamine in 5 ml of dimethylformamide is added in drops, and the reaction mixture is stirred for 2 hours at room temperature. After 100 ml of hexane is added, the precipitated solid is filtered off and purified chromatographically on RP-silica gel LiChroprep$^{(R)}$ RP-8 (Merck), 40–63$\mu$ (eluant: water/MeOH, step gradient of 30% to 90% MeOH); yields: 0.25 g (48%) of 11, 0.35 g (66%) of 12.

EXAMPLES 11 AND 12

Synthesis of 13 and 14 From Dyes 3 and 4

A solution of 0.5 mmol of dye 1 or 2 and 0.1 g (1.0 mmol) of triethylamine in 20 ml of dimethylformamide is mixed at 0° C. with 0.5 mmol of TBTU in 10 ml of dimethylformamide and stirred for 15 minutes at 0° C. Then, a solution of 0.37 g (0.65 mmol) of 6 in 5 ml of dimethylformamide is added in drops, and the reaction mixture is stirred for 18 hours at room temperature. After 100 ml of hexane is added, the precipitated solid is filtered off and purified chromatographically on RP-silica gel LiChroprep$^{(R)}$ RP-8 (Merck), 40–63$\mu$ (eluant: water/MeOH, step gradient of 20% to 80% MeOH); yields: 0.39 g (70%) of 13, 0.41 g (72%) of 14.

The following compounds were obtained analogously by reaction with the described perfluoroalkyl derivatives:

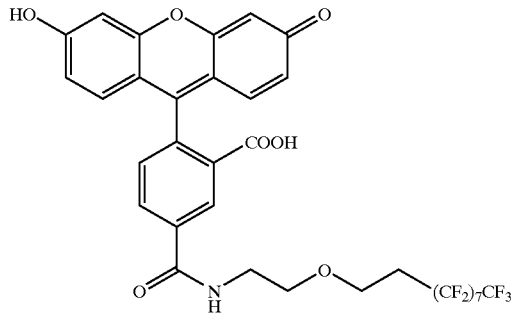

5-Carboxyfluorescein-perfluoroalkylamide

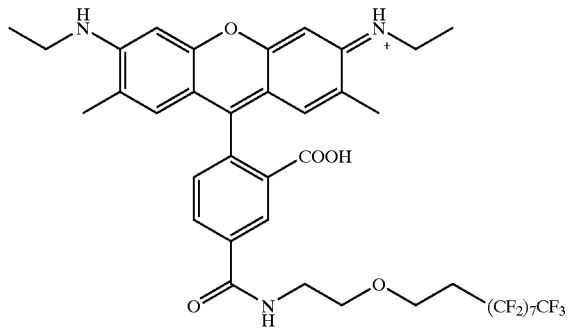

5-Carboxy-rhodamine6G-perfluoroalkylamide

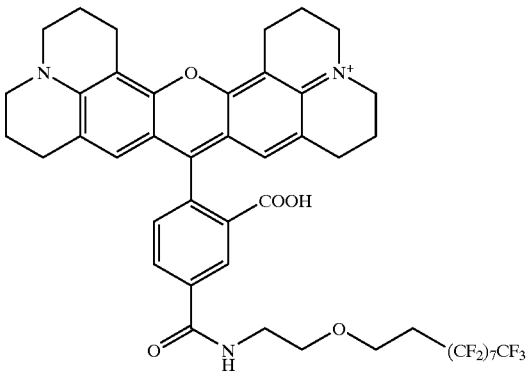

5-Carboxy-X-rhodamine-perfluoroalkylamide

EXAMPLE 13

Production of Galenical Formulations of Gadolinium complex-Perfluoroalkyl Derivatives in the Example of 10-[1-Methyl-2-oxo-3-aza-5-oxo-5-{4-perfluoroctylsulfonyl-piperazin-1-yl}-pentyl]-1,4,7-tris(carboxymethyl)-1,4,7,10-tetraazacyclododecane with 1, 2, 5 and 10 mol % of dyes 7 to 14

118 mg (100 $\mu$mol) of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane (for production, see WO 97/26017, Example 33) is dissolved together with 1 $\mu$mol, 2 $\mu$mol, 5 $\mu$mol or 10 $\mu$mol of 7 to 14 in 50 ml of water for 20 minutes in an ultrasound bath. Then, a dialysis to separate free dyes is performed (Amicon cell, cut-off 10,000, dialysis volumes 5×100 ml). The product solution is set at a volume of 5 ml (20 mmol/l) of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane) with water.

In addition to 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane, the following Gd-complex perfluoroalkyl derivatives were used for the production of the galenical formulations:

Gadolinium complex of 10-[2-hydroxy-4-aza-5-oxo-7-oxa-10,10,11,11,12,12,13,13,14,14,15,15,16,16,17,17,17-heptadecafluoro-heptadecyl]-1,4,7-tris(carboxymethyl)-1,4,7,10-tetraazacyclododecane (for production, see DE 196 03 033, Example 2)

Gadolinium complex of 10-[2-hydroxy-4-aza-5-oxo-7-aza-7-(perfluorooctylsulfonyl)-nonyl]-1,4,7-tris(carboxymethyl)-1,4,7,10-tetraazacyclododecane (for production, see DE 196 03 033, Example 1)

1,4,7-Tris(carboxylatomethyl)-10-[(3-aza-4-oxo-hexan-5-ylic)-acid-N-(1H,1H,2H,2H,4H,4H,5H,5H-3-oxa-perfluorotridecyl)-amide]-1,4,7,10-tetraazacyclododecane, gadolinium complex Production:

10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., and 3.51 (17 mmol) of N,N'-dicyclohexylcarbodiimide is added and stirred for 5 hours at 15° C. To separate the urea, the solution is filtered. 8.63 g (15.88 mmol) of 1H,1H,2H,2H,4H,4H,5H,5H-3-oxa-perfluorotridecylamine, hydrochloride and 5.06 g (50 mmol) of triethylamine are added to the filtrate and stirred for 12 hours at room temperature. The solution is poured into 1,500 ml of diethyl ether/100 ml of acetone and stirred for 30 minutes. The precipitated solid is filtered off and chromatographed on silica gel RP-18 (mobile solvent: gradient that consists of tetrahydrofuran/acetonitrile/water).

Yield: 13.86 g (78% of theory) of a colorless, amorphous powder; Water content: 9.3%; Elementary analysis (relative to anhydrous substance): Cld: C, 33.28 H, 3.42 N, 7.51 F, 28.87 Gd, 14.05. Fnd: C, 33.12 H, 3.61 N, 7.37 F, 28.69 Gd, 13.89.

1,4,7-Tris(carboxylatomethyl)-10-[(3-aza-4-oxo-hexan-5-ylic)-acid-N-(2,3-dihydroxypropyl)-N-(1H,1H,2H,2H,4H,4H,5H,5H-3-oxa)-perfluorotridecyl)-amide]-1,4,7,10-tetraazacyclododecane, gadolinium complex Production:

a) 2H,2H,4H,4H,5H,5H-3—Oxa)-perfluorotridecanoic acid-N-(2,3-dihydroxypropyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution of 5.47 g (60 mmol) of 2,3-dihydroxypropylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/ethanol=15:1).

Yield: 29.70 g (87% of theory) of a colorless solid; Elementary analysis: Cld: C, 30.32 H, 2.20 N, 2.36 F, 54.35. Fnd: C, 30.12 H, 2.41 N, 2.18 F, 54.15.

b) N-(2,3-Dihydroxypropyl)-N-(1H,1H,2H,2H,4H,4H,5H,5H-3-oxa-perfluorotridecyl)-amine 30 g (48.8 mmol) of the title compound of Example a is dissolved in 300 ml of tetrahydrofuran, and 50 ml of 10 M borane dimethyl sulfide (in tetrahydrofuran) is added. It is refluxed for 16 hours. It is cooled to 0° C., and 300 ml of methanol is added in drops, then it is evaporated to the dry state in a vacuum. The residue is taken up in a mixture of 300 ml of ethanol/50 ml of 10% aqueous hydrochloric acid and stirred for 8 hours at 60° C. It is evaporated to the dry state in a vacuum, the residue is taken up in 300 ml of 5% aqueous sodium hydroxide solution and extracted three times with 300 ml of dichloromethane each. The organic phases are dried on magnesium sulfate, evaporated to the dry state in a vacuum, and the residue is chromatographed on silica gel (mobile solvent: dichloromethane/methanol=15:1).

Yield: 24.07 g (85% of theory) of a colorless solid; Elementary-analysis: Cld: C, 31.05 H, 2.61 N, 2.41 F, 55.66. Fnd: C, 31.91 H, 2.78 N, 2.33 F, 55.47.

c) 1,4,7-Tris(carboxylatomethyl)-10-[(3-aza-4-oxo-hexan-5-ylic)-acid-N-(2,3-dihydroxypropyl)-N-(1H,1H,2H,2H,4H,4H,5H,5H-3-oxa)-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.21 (15.88 mmol) of the title compound of Example b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture of 200 ml of acetone/1300 ml of diethyl ether and stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 16.09 g (85% of theory) of a colorless, amorphous powder; Water content: 6.3%; Elementary analysis (relative to anhydrous substance): Cld: C, 34.26 H, 3.64 N, 7.05 F, 27.10 Gd, 13.19. Fnd: C, 34.12 H, 3.83 N, 6.91 F, 26.88 Gd, 12.93.

1,4,7-Tris(carboxylatomethyl)-10-[(3-aza-4-oxo-hexan-5-ylic)-acid-N-(5-hydroxy-3-oxa-pentyl)-N-(1H,1H,2H,2H,4H,4H,5H,5H-3-oxa)-perfluorotridecyl)-amide]-1,4,7,10-tetraazacyclododecane, gadolinium complex Production:

a) 2H,2H,4H,4H,5H,5H-3-Oxa-perfluorotridecanoic acid-N-(5-hydroxy-3-oxa-pentyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane and stirred for 12 hours at room temperature. It is evaporated to the dry state in a vacuum. The residue is dissolved in 100 ml of dichloromethane and added in drops at 0° C. to a solution of 6.25 g (60 mmol) of 5-hydroxy-3-oxa-pentylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 32.20 g (92% of theory) of a colorless solid; Elementary analysis: Cld: C, 31.54 H, 2.65 N, 2.30 F, 53.01. Fnd: C, 31.61 H, 2.84 N, 2.14 F, 52.85.

b) N-(5-Hydroxy-3-oxa-pentyl)-N-(1H,1H,2H,2H,4H,4H,5H,5H-3-oxa-perfluorotridecyl)-amine 30 g (49.24 mmol) of the title compound of Example a is dissolved in 300 ml of tetrahydrofuran, and 31 ml of 10 M borane dimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture of 300 ml of ethanol/50 ml of 10% aqueous hydrochloric acid and stirred for 10 hours at 50° C. It is evaporated to the dry state in a vacuum, the residue is taken up in 300 ml of 5% aqueous sodium hydroxide solution and extracted three times with 300 ml of dichloromethane each. The organic phases are dried on magnesium sulfate, evaporated to the dry state in a vacuum, and the residue is chromatographedon silica gel (mobile solvent: dichloromethane/2-propanol=20:1).

Yield: 26.09 g (89% of theory) of a colorless solid; Elementary analysis: Cld: C, 32.28 H, 3.05 N, 2.35 F, 54.25. Fnd: C, 32.12 H, 3.21 N, 2.18 F, 54.09.

c) 1,4,7-Tris(carboxylatomethyl)-10-[(3-aza-4-oxo-hexan-5-ylic)-acid-N-(5-hydroxy-3-oxa-pentyl)-N-(1H,1H,2H,2H,4H,4H,5H,5H-3-oxa)-perfluorotridecyl)-amide]-1,4,7,10-tetrazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.45 (15.88 mmol) of the title compound of Example b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture of 200 ml of acetone/1300 ml of diethyl ether and stirred for 2 hours at room temperature. The deposited precipitation is filtered off, dissolved in a mixture that consists of a little ethanol/water and chromatographed on silica gel RP-18 (mobile solvent: gradient that consists of tetrahydrofuran/acetonitrile/water).

Yield: 16.10 g (84% of theory) of a colorless, amorphous powder; Water content: 5.7%; Elementary analysis (relative to anhydrous substance): Cld: C, 34.83 H, 3.84 N, 6.96 F, 26.76 Gd, 13.03. Fnd: C, 34.65 H, 3.96 N, 6.84 F, 26.62 Gd, 12.91.

EXAMPLE 14

Production of Galenical Formulations with Monosaccharide-perfluoroalkyl Derivatives in the Example of 6-[1-O-α-D-mannopyranosyl,-hexanoic acid N-(3-oxa-1H,1H,2H,2H,4H,4H,5H,5H-perfluorotridecyl)-amide and Dyes 7 to 14

A) Production of 6-[1-O-α-D-mannopyranosyl]-hexanoic acid N-(3-oxa-1H,1H,2H,2H,4H,4H,5H,5H-perfluorotridecyl)-amide a) 1,2,3,4,6-Penta-o-acetyl-α,β-D-mannopyranose Analogously, as described in the literature [M. L. Wolfrom and A. Thompson in Methods in Carbohydrate Chemistry (R. L. Whistler, M. L. Wolfrom and J. N. BeMiller, Eds.), Academic Press, New York, Vol. II, 53, pp. 211–215, (1963)], the reaction of 150 g (832.5 mmol) of α,β-D-mannopyranose with a mixture that consists of 1,500 ml of absolute pyridine and 1,500 ml of acetic acid anhydride provides, after working-up, 315 g (96.7%) of the above-mentioned title compound as a crude product in the form of a viscous and colorless oil. By $^1$H-NMR-spectroscopic study of the title compound that is thus obtained, the α to β-ratio of both anomers was found to be 4:1. A separation of the α,β-anomers of the above-mentioned title compound can be dispensed with for performing the reaction steps below.

Elementary analysis: Cld: C, 49.21 H, 5.68. Fnd: C, 49.12 H, 5.78.

b) 6-[1-O-α-(2,3,4,6-Tetra-O-acetyl-D-mannopyranosyl)-hexanoic acid ethyl easter]

Analogously, as described in the literature for the synthesis of aryl glycopyranosides [J. Conchie and G. A. Levvy in Methods in Carbohydrate Chemistry (R. L. Whistler, M. L. Wolfrom and J. N. BeMiller, Eds.), Academic Press, New York, Vol. II, 90, pp. 345–347, (1963)], the reaction of 156.2 g (400 mmol) of the title compound of Example Aa) as an α,β-anomer mixture with 67 ml (400 mmol) of 6-hydroxy-hexanoic acid ethyl ester and 60.8 ml (520 mmol) of tin(IV) chloride in a total of 600 ml of 1,2-dichloroethane results in the formation of 100.05 g (51% of theory) of the above-mentioned title compound as a colorless and viscous oil after column-chromatographic purification (eluant: hexane/ethyl acetate 2:1). $^1$H-NMR-spectroscopic study of the title compound that is thus obtained showed that the above-mentioned title compound is only the pure α-anomer.

Elementary analysis: Cld: C, 52.94 H, 6.77. Fnd: C, 52.80 H, 6.78.

c) 6-[1-O-α-(2,3,4,6-Tetra-O-benzyl-D-mannopyranosyl)-hexanoic acid

A stirred suspension of 141.0 g (289 mmol) of the title compound of Example Ab) in 200 ml of dioxane is mixed at room temperature and with simultaneous vigorous stirring in portions with a total of 238.5 g (4.26 mol) of finely powdered potassium hydroxide powder. To increase the stirrability, the reaction mixture is mixed with another 200 ml of dioxane, and the suspension that is thus obtained is subsequently heated to boiling and mixed drop by drop at this temperature with a total of 372 ml (3.128 mol) of benzyl bromide over a period of two hours. After a reaction time of 4 hours at 110° C. followed by 12 hours at room temperature, the reaction mixture is slowly poured into a total of 2.5 liters of ice water for the purpose of working-up, and the water phase is subsequently completely extracted with diethyl ether. After the ether phase that is thus obtained is washed and the same is subsequently dried on sodium sulfate, salt is suctioned out, and the diethyl ether is removed in a vacuum. Excess benzyl bromide is then quantitatively distilled off from the reaction mixture in an oil pump vacuum at an oil bath temperature of 180° C. The resinous-oily residue that is thus obtained is purified on silica gel with use of ethyl acetate/hexane (1:10) as an eluant.

Yield: 172.2 g (91.0% of theory) of the above-mentioned title compound in the form of a colorless and extremely viscous oil; Elementary analysis: Cld: C, 75.68 H, 7.16. Fnd: C, 75.79 H, 7.04.

d) 6-[1-O-α-(2,3,4,6-Tetra-O-benzyl-D-mannopyranosyl)-hexanoic acid-N-(3-oxa-1H,1H,2H,2H,4H,4H,5H,5H-perfluorotridecyl)-amide 100 g (134 mmol) of the acid that is described in Example Ac) and 13.5 g (134 mmol) of triethylamine are dissolved in 1,200 ml of dry tetrahydrofuran. After cooling to −15° C., a solution of 18.45 g (135 mmol) of isobutyl chloroformate in 200 ml of dry tetrahydrofuran is slowly added in drops while being stirred, whereby the internal temperature does not exceed −10° C. After a reaction time of 15 minutes at −15° C., a solution of 165.5 g (134 mmol) of 1-amino-1H,1H,2H,2H-perfluorodecane and 13.5 g (134 mmol) of triethylamine in 250 ml of dry tetrahydrofuran are added in drops at −20° C. After a reaction time of one hour at −15° C. and two hours at room temperature, the reaction solution is evaporated to the dry state in a vacuum. The remaining residue is taken up in 300 ml of ethyl acetate and washed twice with 400 ml of saturated sodium bicarbonate solution each and once with 500 ml of water. After the organic phase is dried on sodium sulfate, salt is suctioned out, and the ethyl acetate is removed in a vacuum. The remaining oily residue is purified on silica gel with use of dichloromethane/hexane/2-propanol (10:5:1) as an eluant.

Yield: 143.8 g (86.9% of theory); Elementary analysis: Cld: C, 57.38 H, 4.98 N, 1.13 F, 26.15. Fnd: C, 57.30 H, 5.44 N, 1.01 F, 26.25.

e) 6-[1-O-α-D-Mannopyranosyl)-hexanoic acid N-(3-oxa-1H,1H,2H,2H,4H,4H,5H,5H-perfluorotridecyl)-amide 40.0 g (32.38 mmol) of the title compound of Example Ad) is dissolved in 750 ml of 2-propanol and mixed with 2.0 g of palladium catalyst (10% Pd/C). The reaction solution is hydrogenated for 12 hours at 22° C. and 1 atmosphere of hydrogen pressure.

Then, catalyst is filtered off, and the filtrate is evaporated to the dry state. The remaining residue is taken up in 300 ml of dimethyl sulfoxide, and 21.52 g (88.0% of theory) of the above-mentioned title compound is obtained as a colorless and crystalline powder with the decomposition melting point of 88.5° C. from the product solution that is thus obtained by mixing with a total of 1000 ml of diethyl ether after the precipitated solution is suctioned off.

Elementary analysis: Cld: C, 36.01 H, 5.92 N, 1.75 F, 40.34. Fnd: C, 36.07 H, 6.08 N, 1.76 F, 40.66.

B) Production of the Formulation

100 μmol of 6-[1-O-α-D-mannopyranosyl)-hexanoic acid N-(3-oxa-1H,1H,2H,2H,4H,4H,5H,5H-perfluorotridecyl)-amide is dissolved in 0.5 ml of ethanol, then mixed with 50 ml of water, and 1, 2, 5 and 10 mol % of dyes 7 to 14 are added in solid form. After 1 hour of treatment in an ultrasound bath, dialysis is carried out as described in Example 13.

In addition to 6-[1-O-α-D-mannopyranosyl)-hexanoic acid N-(3-oxa-1H,1H,2H,2H,4H,4H,5H,5H-perfluorotridecyl)-amide, the following monosaccharide-perfluoroalkyl derivatives I–III can be used for the production of galenical formulations:

I. 1-O-α-D-[(1-Perfluorooctylsulfonyl-piperazine-4-carbonyl)-pentyl-5]-mannopyranose a) 1-O-α-D-[(1-Perfluorooctylsulfonylpiperazine-4-carbonyl)-pentyl-5]-2,3,4,6-tetra-O-benzyl-mannopyranose 74.59 g (100 mmol) of the acid that is described in Example Ac) and 10.11 g (100 mmol) of triethylamine are dissolved in 800 ml of a mixture of tetrahydrofuran/acetonitrile (mixing ratio 7:3). Then, it is mixed drop by drop at room temperature with 500 ml of a tetrahydrofuran solution of 58.0 g (102.0 mmol) of 1-perfluorooctyl-sulfonylpiperazine; 10,11 g (100 mmol) of triethylamine and 16.84 g (110 mmol) of 1-hydroxybenzotriazole. The reaction solution that is thus obtained is mixed at −5° C. with a solution of 22.7 g (110 mmol) of dicyclohexylcarbodiimide, dissolved in 100 ml of tetrahydrofuran, and then stirred at −5° C. for two more hours. After the reaction solution has thawed, it is stirred at room temperature for another 12 hours, precipitated dicyclohexylurea is filtered out, and the filtrate that is obtained is evaporated to the dry state in a vacuum. The remaining residue is taken up in 600 ml of ethyl acetate and washed twice with 300 ml of saturated sodium bicarbonate solution each as well as twice with 300 ml of water each.

After the organic phase is dried on sodium sulfate, salt is suctioned out, and the ethyl acetate is removed in a vacuum. The remaining oily residue is purified on silica gel with use of dichloromethane/acetone/2-propanol (16:2:1) as an eluant.

Yield: 113.01 g (79.8% of theory) of a colorless and viscous oil; Elementary analysis: Cld: C, 58.52 H, 4.27 N, 1.98 S, 2.26 F, 22.80. Fnd: C, 58.42 H, 4.41 N, 1.80 S, 2.28 F, 23.02.

b) 1-O-α-D-[(1-Perfluorooctylsulfonyl-piperazine-4-carbonyl)-pentyl-5]-mannopyranose 50 g (35.30 mmol) of the title compound of Example Ia) is dissolved in a mixture that consists of 500 ml of 2-propanol and 50 ml of water, and 2 g of palladium catalyst (10% Pd on activated carbon) is added. It is hydrogenated for 12 hours at room temperature. Catalyst is filtered out, and the filtrate is evaporated to the dry state in a vacuum. The residue is dissolved in 200 ml of methanol, and the reaction product is precipitated by mixing with a total of 800 ml of diethyl ether. After the solid that is thus obtained is suctioned off, the latter is dried in a vacuum at 50° C.

Yield: 29.51 g (99% of theory) of an amorphous solid; Elementary analysis: Cld: C, 34.13 H, 3.46 N, 3.32 S, 3.80 F, 38.23. Fnd: C, 34.28 H, 3.81 N, 3.25 S, 3.80 F, 38.01.

II. 2-Deoxy-2-[acetyl-(2-amino-N-ethyl-N-perfluorooctylsulfonyl)-amino]-1-α,β-D-mannopyranose a) 2-Acetamido-2-deoxy-1,3,4,6-(tetra-O-benzyl)-α,β-D-glucopyranose A total of 24.0 g (108.5 mmol) of 2-acetamido-2-deoxy-α,β-D-glucopyranose, dissolved in 500 ml of absolute dimethyl sulfoxide, is added drop by drop at room temperature to a stirred suspension of 20.16 g (700 mmol/80% in mineral oil) of sodium hydride in 150 ml of dimethyl sulfoxide. Then, it is allowed to stir for 120 more minutes at room temperature, and then 159.5 g (1.26 mol) of benzyl chloride is added in drops. The reaction solution that is thus obtained is subsequently stirred for another 12 hours at room temperature. For working-up, the reaction solution is slowly poured into 1.5 liters of ice water and then exhaustively extracted with diethyl ether. The combined diethyl ether phases are subsequently washed twice with 600 ml of saturated sodium bicarbonate solution each and twice with 800 ml of water each. After the organic phase is dried on sodium sulfate, salt is suctioned out, and the solvent is removed in a vacuum. The remaining oily residue is purified on silica gel with use of ethyl acetate/hexane (1:5) as an eluant.

Yield: 48.68 g (73.6% of theory) of the above-mentioned title compound in the form of a viscous and colorless oil; Elementary analysis: Cld: C, 70.92 H, 6.45 N, 6.89. Fnd: C, 71.43 H, 6.44 N, 7.02.

b) 1-O-Benzyl-3,4,6-tri-O-benzyl-2-amino-2-deoxy-α,β-D-glucopyranose 30.0 g (49.2 mmol) of the title compound of Example IIa) is suspended in a mixture of 750 ml of methanol and 215 ml of water and mixed drop by drop at room temperature with a total of 440 ml (49.2 mmol) of a 0.112 molar aqueous perchloric acid solution. After the addition is completed, the reaction solution is stirred for 10 more minutes at room temperature, and the now homogenous reaction solution that is thus obtained is subsequently evaporated to the dry state in a vacuum. By mixing the remaining oily residue with a mixture that consists of equal parts of hexane and dichloromethane, the latter is crystallized. The crystalline reaction product is suctioned off, washed with hexane and dried in a vacuum at room temperature.

Yield: 27.08 g (86% of theory) of the above-mentioned title compound in the form of its perchlorate, which is present as a colorless, crystalline compound.

Melting point: 180.5–181.5° C.; Elementary analysis: Cld: C, 63.68 H, 5.98 N, 2.19 Cl, 5.54. Fnd: C, 63.43 H, 6.04 N, 2.02 Cl, 5.71.

c) 1,3,4,6-Tetra-O-benzyl-2-deoxy-2-[acetyl-(2-amino-N-ethyl-N-perfluorooctylsulfonyl)-amino]-1-α,β-D-mannopyranose 20.8 g (35.6 mmol) of the 2-[N-ethyl-N-perfluorooctylsulfonyl]-aminoacetic acid and 3.60 g (35.6 mmol) of triethylamine are dissolved in 350 ml of dry tetrahydrofuran. After the reaction solution is cooled to −15° C. to −20° C., a solution of 4.92 g (35.6 mmol) of isobutyl chloroformate in 75 ml of dry tetrahydrofuran is slowly added in drops at this temperature while being stirred, whereby the dropwise addition rate is to be selected so that an internal temperature of −10° C. is not exceeded. After a reaction time of 15 minutes at −15° C., a solution of 22.78 g (35.6 mmol) of the perchlorate (title compound of Example IIb) and 3.60 g (35.6 mmol) of triethylamine, in 100 ml of dry tetrahydrofuran, is then slowly added in drops at −20° C. After a reaction time of one hour at −15° C. and two hours at room temperature, the reaction solution is evaporated to the dry state in a vacuum. The remaining residue is taken up in 250 ml of ethyl acetate and washed twice with 100 ml of saturated sodium bicarbonate solution each and once with 200 ml of water. After the organic phase is dried on sodium sulfate, salt is suctioned out, and the ethyl acetate is removed in a vacuum. The remaining oily residue is purified on silica gel with use of ethyl acetate/hexane (1:5) as an eluant.

Yield: 33.3 g (84.6% of theory) of the above-mentioned title compound as a colorless and strongly viscous oil; Elementary analysis: Cld: C, 49.92 H, 3.92 N, 2.53 F, 29.18 S, 2.90. Fnd: C, 49.99 H, 4.11 N, 2.69 F, 29.22 S, 3.01.

d) 2-Deoxy-2-[acetyl-(2-amino-N-ethyl-N-perfluorooctylsulfonyl)-amino]-1-α,β-D-mannopyranose 20.0 g (18.06 mmol) of the title compound of Example IIc) is dissolved in 250 ml of 2-propanol and mixed with 1.5 g of palladium catalyst (10% Pd/C). The reaction solution is hydrogenated for 12 hours at 22° C. and 1 atmosphere of hydrogen pressure. Then, catalyst is filtered out, and the filtrate is evaporated to the dry state. The remaining residue is taken up in 300 ml of dimethyl sulfoxide, and 12.65 g (93.8% of theory) of the above-mentioned title compound is obtained as a colorless and crystalline powder from the product solution that is thus obtained by mixing with 750 ml of a mixture that consists of equal parts of dimethyl ether and ethyl acetate after the precipitated solid is suctioned off. The above-mentioned title compound is present as an α/β-anomer mixture, whereby the ratio relative to the two possible anomers was determined at about 1:1.2 by $^1$H-NMR-spectroscopic studies. Accordingly, the title compound is an almost approximately evenly divided α/β-anomer mixture.

Melting point: 132.5–133° C. Elementary analysis: Cld: C, 28.97 H, 2.57 N, 3.75 F, 43.27 S, 4.30. Fnd: C, 29.09 H, 2.56 N, 3.84 F, 43.36 S, 4.42.

III. 1-O-β-D-[6-Hexanoic acid-N-(3-oxa-1H,1H,2H,2H,4H,4H,5H,5H-perfluorotridecyl)-amide]-glucopyranose a) 1,2,3,4,6-Penta-O-acetyl-α-D-glucopyranose Analogously, as described in the synthesis of title compound Aa), the reaction of 100 g (555.0 mmol) of α-D-glucopyranose with a mixture of 1000 ml of absolute pyridine and 1000 ml of acetic acid anhydride after working-up and recrystallization from 95% aqueous ethanol yields 190.6 g (88.0%) of the above-mentioned title compound as a colorless and crystalline compound. By $^1$H-NMR-spectroscopic study of the title compound that is thus obtained, it was possible to determine the α to β-ratio of two possible anomers with ≧98:2. Accordingly, the title compound is the exclusively α-configured anomer.

Melting point: 110.5° C.; Elementary analysis: Cld: C, 49.21 H, 5.68. Fnd: C, 49.24 H, 5.68.

b) 5-(Ethoxycarbonyl)pentyl-2,3,4,6-tetra-O-acetyl-α-D-mannopyranoside

Analogously, as described in the synthesis of the title compound of Example Ab), the reaction of 130.0 g (332.8 mmol) of the title compound of Example IIIa) with 55.8 ml (332.8 mmol) of 6-hydroxy-hexanoic acid ethyl ester and 50.6 ml (520 mmol) of tin(IV) chloride in 500 ml of 1,2-dichloroethane after column-chromatographic working-up (eluant: hexane/ethyl acetate 2:1) yields 101.85 g (62.4% of theory) of the above-mentioned title compound as a colorless and viscous oil. After $^1$H-NMR-spectroscopic study of the title compound, the presence of the β-configuration at the anomeric center was definitively established based on the size of the coupling constant of $J_{1,2}$=8.8 Hz; moreover, said configuration represents the sole existing configuration at the anomeric center. It was thus possible to depict the above-mentioned title compound only in the form of the β-configured anomer.

Elementary analysis: Cld: C, 52.94 H, 6.77. Fnd: C, 52.77 H, 6.70.

c) 5-(Carboxyypentyl-2,3,4,6-tetra-O-benzyl-α-D-mannopyranoside

A stirred suspension of 100.0 g (204.96 mmol) of the title compound of Example IIIb) in 150 ml of dioxane is mixed at room temperature and with simultaneous, vigorous stirring in portions with a total of 169.14 g (3.02 mol) of finely powdered potassium hydroxide powder. To increase the stirrability, the reaction mixture is mixed with another 150 ml of dioxane, and the suspension that is thus obtained is subsequently heated to boiling and mixed drop by drop at this temperature with a total of 264 ml (2.218 mol) of benzyl bromide over a period of two hours. After a reaction time of 4 hours at 110° C. followed by 12 hours at room temperature, the reaction mixture is slowly poured into a total of 2.0 liters of ice water for the purpose of working-up, and the water phase is subsequently completely extracted with diethyl ether. After the ether phase that is thus obtained is washed and said phase is subsequently dried on sodium sulfate, salt is suctioned out, and the diethyl ether is removed in a vacuum. Excess benzyl bromide is then quantitatively distilled off from the reaction mixture in an oil pump vacuum at an oil bath temperature of 180° C. The remaining oily residue that is thus obtained is purified on silica gel with use of ethyl acetate/hexane (1:10) as an eluant.

Yield: 128.8 g (84.3% of theory) of the above-mentioned title compound in the form of a colorless and extremely viscous oil; Elementary analysis: Cld: C, 75.68 H, 7.16. Fnd: C, 75.66 H, 7.23.

d) 2,3,4,6-Tetra-O-benzyl-1-O-β-D-[6-hexanoic acid-N-(3-oxa-1H,1H,2H,2H,4H,4H,5H,5H-perfluorotridecyl)-amide]-glucopyranose 68.5 g (91.79 mmol) of the acid that is described in Example IIIc) and 9.25 g (91.79 mmol) of triethylamine are dissolved in 825 ml of dry tetrahydrofuran. After the reaction solution is cooled to −15° C. to −20° C., a solution of 12.64 g (92.5 mmol) of isobutyl chloroformate in 150 ml of dry tetrahydrofuran is slowly added in drops at this temperature while being stirred, whereby the dropwise addition rate is to be selected such that an internal temperature of −10° C. is not exceeded. After a reaction time of 15 minutes at −15° C., a solution of 46.40 g (91.79 mmol) of 1H,1H,2H,2H-heptadecafluoro-1-(2-aminoethyoxy)-decane and 9.25 g (91.79 mmol) of triethylamine is then slowly added in drops at −20° C. as a solution in 200 ml of dry tetrahydrofuran. After a reaction time of one hour at −15° C., and two hours at room temperature, the reaction solution is evaporated to the dry state in a vacuum. The remaining residue is taken up in 250 ml of ethyl acetate and washed twice with 300 ml of saturated sodium bicarbonate solution each and once with 400 ml of water. After the organic phase is dried on sodium sulfate, salt is suctioned out, and the ethyl acetate is removed in a vacuum. The remaining oily residue is purified on silica gel with use of dichloromethane/hexane/2-propanol (10:5:1) as an eluant.

Yield: 104.7 g (92.4% of theory) of the above-mentioned title compound as a colorless and strongly viscous oil. Elementary analysis: Cld: C, 57.38 H, 4.98 N, 1.13 F, 26.15. Fnd: C, 57.27 H, 5.09 N, 1.11 F, 26.08.

e) 1-O-β-D-[6-Hexanoic acid-N-(3-oxa-1H,1H,2H,2H,4H,4H,5H,5H-perfluorotridecyl)-amide]-glucopyranose 40.0 g (32.38 mmol) of the title compound of Example IIId) is dissolved in 750 ml of 2-propanol and mixed with 2.0 g of palladium catalyst (10% Pd/C). The reaction solution is hydrogenated for 12 hours at 22° C. and 1 atmosphere of hydrogen pressure. Then, catalyst is filtered out, and the filtrate is evaporated to the dry state. The remaining residue is taken up in 300 ml of dimethyl sulfoxide and 22.05 g (90.2% of theory) of the title compound is obtained as a colorless and crystalline powder with a decomposition melting point of 122–124° C. from the product solution that is thus obtained by mixing with a total of 1000 ml of diethyl ether and subsequent suctioning-off of the precipitated solid.

Elementary analysis: Cld: C, 36.01 H, 5.92 N, 1.75 F, 40.34. Fnd: C, 36.07 H, 6.08 N, 1.76 F, 40.66.

EXAMPLE 15

Production of Galenical Formulations of Three Components in the Example of 6-[1-O-α-D-Mannopyranosyl)-Hexanoic Acid N-(3-oxa-1H,1H,2H,2H,4H,4H,5H,5H-perfluorotridecyl)-amide, 10-[1-Methyl-2-oxo-3-aza-5-oxo-5-{4-Perfluorooctylsulfonyl-piperazin-1-yl}-Pentyl]-1,4,7-tris(Carboxymethyl)-1,4,7,10-Tetraazacyclododecane and Dyes 7 to 14

The production was performed analogously to the general instructions of Example 14 with use of various proportions of 6-[1-O-α-D-mannopyranosyl)-hexanoic acid N-(3-oxa-1H,1H,2H,2H,4H,4H,5H,5H-perfluorotridecyl)-amide and 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane, and of 5 mol % of dyes 7 to 14 in each case. In this case, 6-[1-O-α-D-mannopyranosyl)-hexanoic acid N-(3-oxa-1H,1H,2H,2H,4H,4H,5H,5H-perfluorotridecyl)-amide was dissolved in ethanol, mixed with a solution of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane in water, and the mixture was treated in an ultrasound bath after dye was added, and the procedure was as in Example 13.

EXAMPLE 16

Photophysical Characterization of the Formulations

The determination of the absorption maxima and extinction coefficients was carried out with a Lambda 2-spectrometer (Perkin-Elmer Company). The fluorescence properties were determined on a SPEX-fluorolog (Instruments S. A. Company, photomultiplier Hamamatsu PM928, excitation 350W xenon lamp). the determination of the fluorescence quantum yield was carried out relative to indocyanine green (O=13% in DMSO) by excitation at 585 nm (dyes with p=2) or 685 nm (dyes with p=3), in each case of solutions of concentration 2 μM in dye, and correction with the spectral sensitivity of lamp and detector.

Absorption and fluorescence properties of formulations with 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane depending on the dye proportion in the example of dyes 7 and 8

| Dye | Mol % of dye | Absorption max. (nm) | Extinction coefficient (L mol$^{-1}$ cm$^{-1}$) | Fluorescence max. (nm) | Fluorescence quantum yield |
|---|---|---|---|---|---|
| 7 | 1 | 652 | 132,000 | 681 | 0.17 |
| 7 | 2 | 651 | 130,200 | 683 | 0.18 |
| 7 | 5 | 651 | 123,700 | 685 | 0.12 |
| 7 | 10 | 649 | 110,900 | 685 | 0.04 |
| 8 | 1 | 755 | 150,500 | 784 | 0.23 |
| 8 | 2 | 755 | 148,800 | 785 | 0.23 |
| 8 | 5 | 753 | 120,800 | 788 | 0.14 |
| 8 | 10 | 751 | 108,500 | 790 | 0.03 |

Absorption and fluorescence properties of the galenical formulation with 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane and dyes 7–14 in a proportion of 5 mol %

| Dye | Mol % of dye | Absorption max. (nm) | Extinction coefficient (L mol$^{-1}$ cm$^{-1}$) | Fluorescence max. (nm) | Fluorescence quantum yield |
|---|---|---|---|---|---|
| 7 | 5 | 651 | 123,700 | 685 | 0.12 |
| 8 | 5 | 753 | 120,800 | 788 | 0.14 |
| 9 | 5 | 653 | 145,000 | 683 | 0.14 |
| 10 | 5 | 754 | 118,800 | 788 | 0.13 |
| 11 | 5 | 650 | 150,700 | 684 | 0.16 |
| 12 | 5 | 753 | 124,100 | 789 | 0.09 |
| 13 | 5 | 653 | 139,400 | 682 | 0.12 |
| 14 | 5 | 754 | 120,900 | 789 | 0.11 |

Absorption and fluorescence properties of the galenical formulations with 6-[1-O-α-D-mannopyranosyl)-hexanoic acid N-(3-oxa-1H,1H,2H,2H,4H,4H,5H,5H-perfluorotridecyl)-amide, 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane and dye 8 in a proportion of 5 mol %

| Dye | Mol % of dye | Mol % of Gd complex | Mol % of monosaccharide | Absorption maximum (nm) | Extinction coefficient (L mol$^{-1}$ cm$^{-1}$) | Fluorescence maximum (nm) | Fluorescence quantum yield |
|---|---|---|---|---|---|---|---|
| 8 | 5 | 0 | 95 | 760 | 90500 | 800 | 0.16 |
| 8 | 5 | 10 | 85 | 760 | 102700 | 800 | 0.11 |
| 8 | 5 | 30 | 65 | 760 | 107900 | 800 | 0.14 |
| 8 | 5 | 50 | 45 | 756 | 108700 | 798 | 0.26 |
| 8 | 5 | 70 | 25 | 756 | 111100 | 794 | 0.18 |
| 8 | 5 | 90 | 5 | 755 | 112500 | 793 | 0.13 |

EXAMPLE 17

Production of Lyophilizates and Resuspension

The galenical formulations that are produced according to the instructions of Examples 13 to 15 are freeze-dried according to common procedures. The blue-colored lyophilizates are stored for 5 days at room temperature, then resuspended by shaking in 5–10 ml of water and subjected to dialysis as described above. The dye content after dialysis was determined photometrically and in all cases amounted to 96–99% relative to the content before freeze-drying and resuspension.

EXAMPLE 18

Interstitial Near-infrared Lymphography of Guinea Pigs with a Formulation with 5 mol % of Dye 8/95 mol % of 10-[1-Methyl-2-oxo-3-aza-5-oxo-5-{4-Perfluorooctylsulfonyl-piperazin-1-yl}-Pentyl]-1,4,7-tris(Carboxymethyl)-1,4,7,10-tetraazacyclododecane The imaging properties of the formulations according to the invention were studied in vivo in guinea pigs. In this respect, a formulation was administered interstitially/intracutaneously, and the concentration in regional lymph nodes was observed in a period of 0 to 120 minutes. The fluorescence of the substances was stimulated by irradiation of the animals with near-infrared light of wavelength 740 nm, which was produced with an Nd:YAG laser. The fluorescence radiation was detected at a wavelength of >800 nm by an intensified CCD-camera, and the fluorescence images were stored digitally.

Figure 1B:
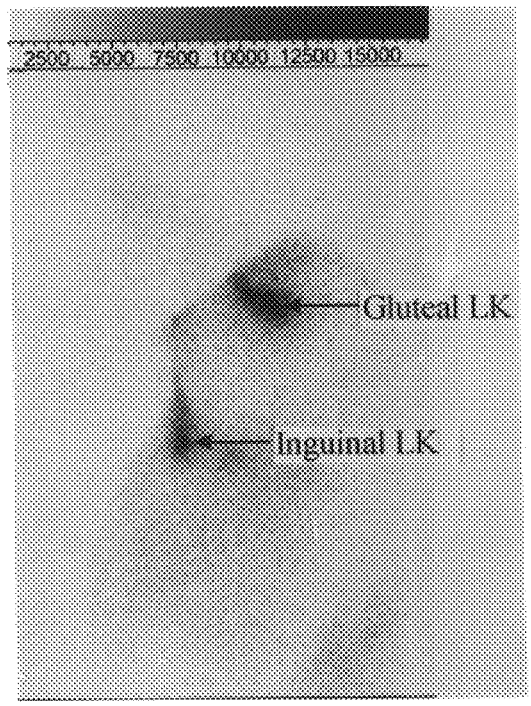

FIG. 1 shows near-infrared fluorescence images of a guinea pig after interstitial/intracutaneous administration of formulations with 5 mol % of dye 8/95 mol % of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane. 0.1 ml of a stock solution with 1 mmol/L of 8 was injected into a skin fold between the toes of the right rear extremity, and the final concentration was 0.3 μmol/kg of 8.

A. Abdominal view, 120 minutes after administration, the right rear foot of the animal was covered during imaging, since the injection site had a strong fluorescence signal.

B. Right lateral view, 117 minutes after administration, the right rear leg of the animal was covered in the imaging, since the injection site had a strong fluorescence signal.

EXAMPLE 19

Coloring of Regional Lymph Nodes after Interstitial Administration of a Formulation with 5 mol % of Dye 8/95 mol % of 10-[1-Methyl-2-oxo-3-aza-5-oxo-5-{4-Perfluorooctylsulfonyl-piperazin-1-yl}-Pentyl]-1,4,7-tris(Carboxymethyl)-1,4,7,10-tetraazacyclododecane After the interstitial near-infrared lymphography was completed, the regional lymph nodes were prepared in the area of the administration site. It was observed that these lymph nodes have a green coloring because of the accumulation of the substance according to the invention. This coloring can be used for the intraoperative diagnosis for the identification of the draining lymph nodes of a certain tissue area and for differentiating the lymph nodes from the surrounding tissue.

Figure 2:
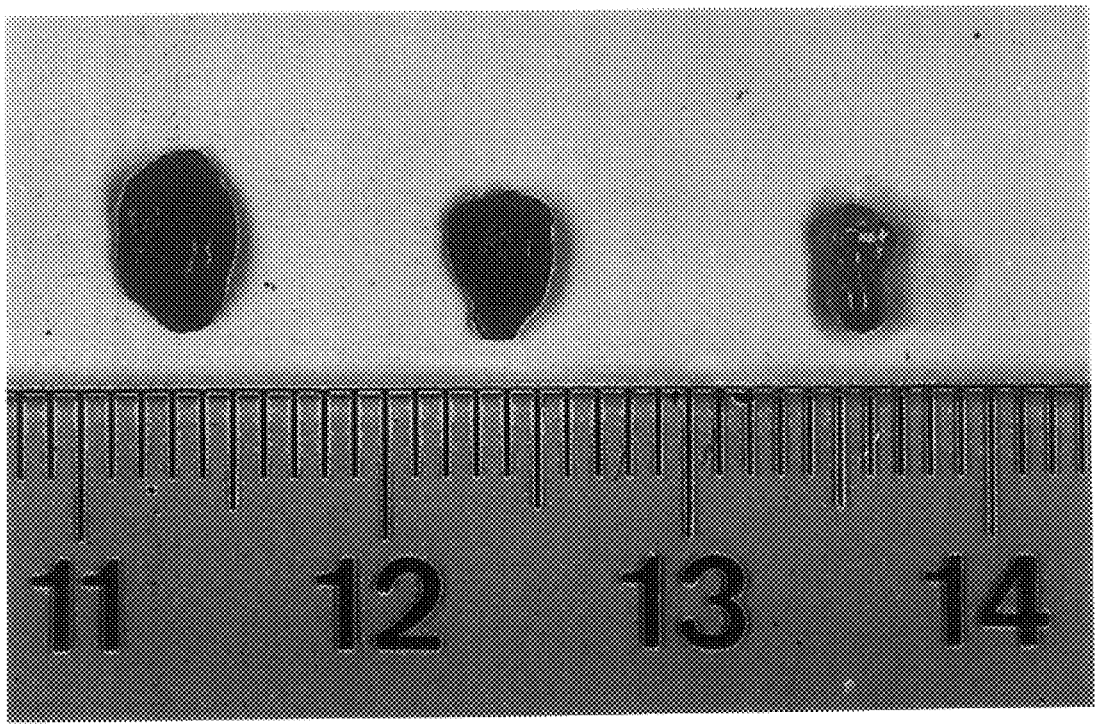
FIG. 2 shows two inguinal lymph nodes of guinea pigs after interstitial/intracutaneous administration of a formulation, see Example 19.
Figure 3A:
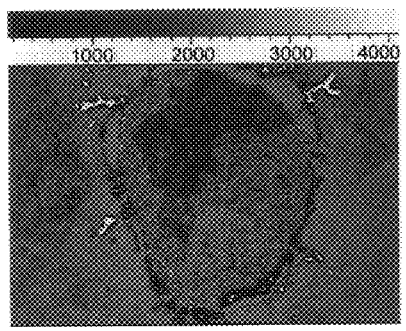
FIG. 3 shows a bright-field (3a) and a near-infrared-fluorescence image (3b) of a frozen section of a popliteal guinea pig lymph node four hours after interstitial administration of a formulation, and shows shows a bright-field (3c) and a near-infrated-fluorescence image (3d) of a cryo-section of a popliteal lymph node of an untreated guinea pig, see Example 20.
Figure 3B:
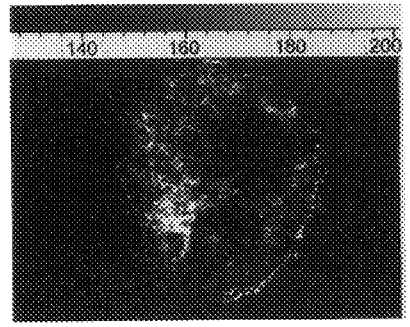
Figure 3C:
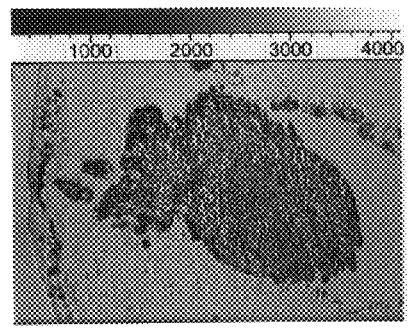
Figure 3D:
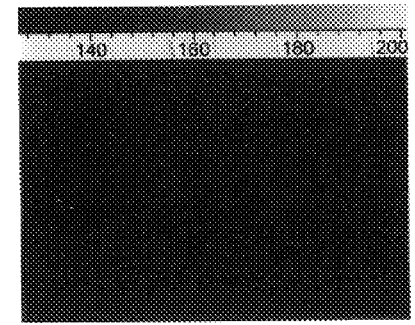

FIG. 2 shows two inguinal lymph nodes of guinea pigs after interstitial/intracutaneous administration of a formulation with 5 mol % of dye 8/95 mol % of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane (A, B) and a lymph node of an untreated guinea pig ex vivo (C). A formulation with 5 mol % of dye 8 resulted in a clearly visible green-coloring of the lymph nodes after interstitial administration.

EXAMPLE 20

Localization of the Formulation with 5 mol % of Dye 8/95 mol % of 10-[1-Methyl-2-oxo-3-aza-5-oxo-5-{4-perfluorooctylsulfonyl-piperazin-1-yl}-Pentyl]-1,4,7-tris(carboxymethyl)-1,4,7,10-tetraazacyclododecane in Lymph Nodes The localization of the formulations according to the invention in lymph nodes was studied by fluorescence microscopy on frozen sections of the lymph nodes. In this respect, the lymph nodes were prepared after the lymphography and deep-frozen at −80° C. Sections with a 5 μm thickness were produced on a freezing microtome. The evaluation was carried out on a Zeiss Axiovert 135-fluorescence microscope, which was equipped with a Cy 7-(excitation filter HQ710/70 nm, emission filter 810/90 nm, beam splitter 750 nm LP). From all the preparations, white light and fluorescence images were recorded with a CCD camera (Princeton Instruments RTE/CCD-576) and stored digitally.

FIG. 3 shows a bright-field (3a) and a near-infrared-fluorescence image (3b) of a frozen section of a popliteal guinea pig lymph node four hours after interstitial administration of a formulation with 5 mol% of dye 8/95 mol% of 10-[1-methyl-2-oxo-3-aza-5-oxo-5-{4-perfluorooctylsulfonyl-piperazin-1-yl}-pentyl]-1,4,7-tris (carboxymethyl)-1,4,7,10- tetraazacyclododecane. Images of a cryosection from a popliteal lymph node of an untreated guinea pig in bright field (3c) and in near-infrared-fluorescence (3d) are shown for comparison. Lymph nodes from guinea pigs that had received an interstitial/intracutaneous injection of the formulation showed a pronounced fluorescence in the near-infrared wavelength range, while the lymph nodes of untreated animals have no fluorescence.

Image parameters:

Bright field: Lens 2.5×. Exposure 0.02 seconds, no accumulation. Tube enlargement 0.6.

NTR: Lens 2.5×. Exposure 1 second, accumulation 5×, tube enlargement 0.6, Cy7-set of filters.

EXAMPLE 21

Fluorescence Coloring of Lymph Nodes After Intravenous Administration of a Formulation with 5 mol % of Dye 8 and 95 mol % of 10-[1-Methyl-2-oxo-3-aza-5-oxo-5-{4-Perfluorooctylsulfonyl-piperazin-1-yl}-Pentyl]-1,4,7-tris(Carboxymethyl)-1,4,7,10-tetraazacyclododecane From the substance, 0.2 ml of a solution that contained 0.5 mmol/L of dye 8 and 9.5 mmol/L of 10-[1-methyl-2-oxo-3-aza-5-oxo-5-{4-perfluorooctylsulfonyl-piperazin- 1-yl}-pentyl]-1,4,7-tris(carboxymethyl)-1,4,7,10-tetraazacyclododecane, was administered intravenously in a caudal vein of the rat. Five hours after administration, the lymph nodes were prepared and a fluorescence image was recorded. The fluorescence of the substances was stimulated by irradiation of the lymph nodes with near-infrared light of wavelength 740 nm, which was produced with an Nd:YAG laser. The fluorescence radiation was detected at a wavelength of >800 nm by an intensified CCD-camera, and the fluorescence images were stored digitally.

Figure 4:
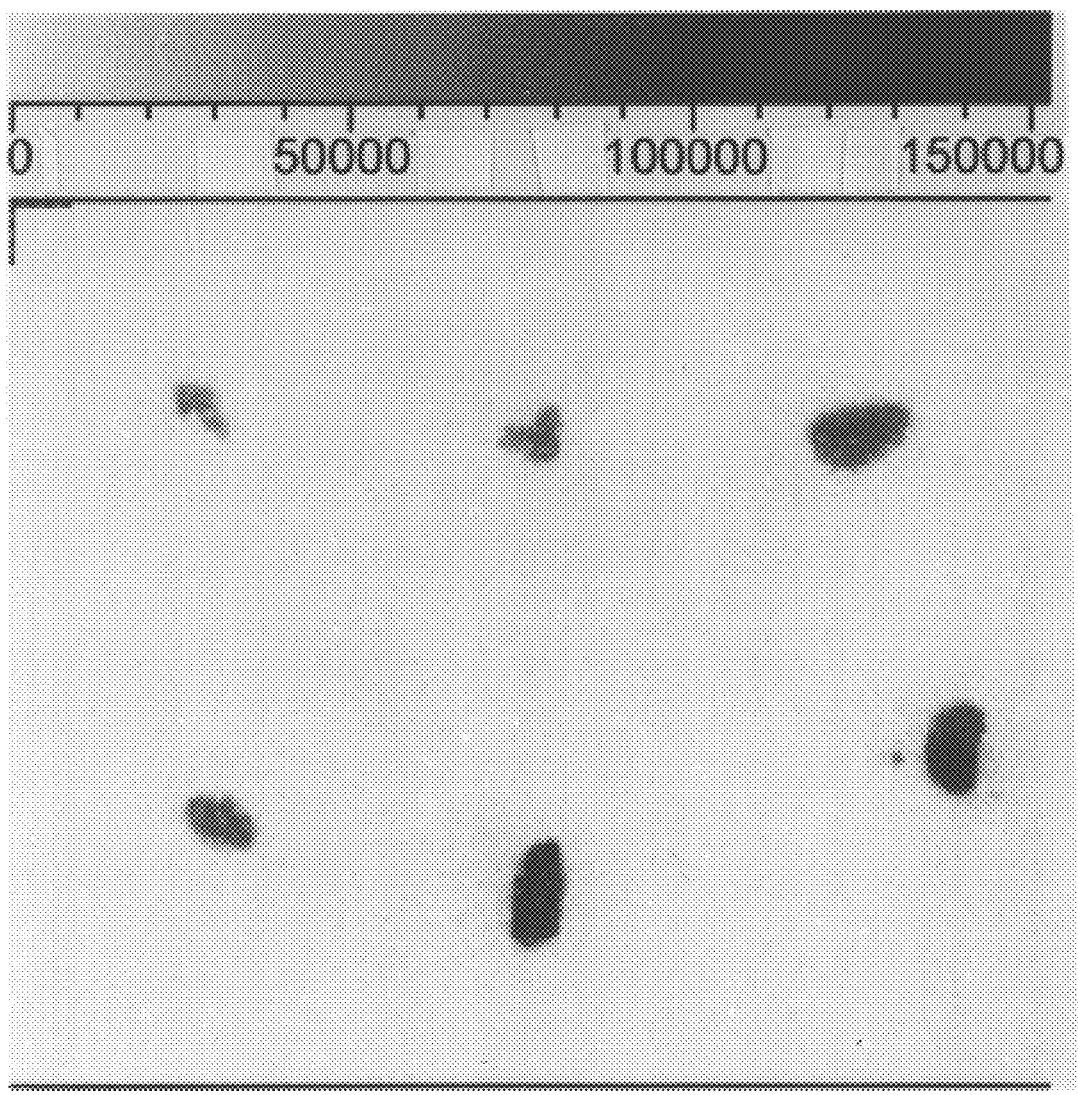
FIG. 4 shows a fluorescence image of lymph nodes five hours after intravenous administration of a formulation, see Example 21.

FIG. 4 shows a fluorescence image of lymph nodes 5 hours after intravenous administration of a formulation with 5 mol % of dye 8 and 95 mol % of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane. Shown are the axillary (a, a'), inguinal (b, b') and popliteal (c, c') lymph nodes of the animal. All lymph nodes showed a clear fluorescence signal.

EXAMPLE 22

Visualization of Lymph Nodes in Situ After Interstitial Administration of a Formulation with 5 mol % of Dye 8 and 95 mol % of 6-[1-O-α-D-Mannopyranosyl)-hexanoic Acid N-(3-oxa-1H,1H, 2H,2H,4H,4H,5H,5H-perfluorotridecyl)-amide in Rats 0.1 ml of a formulation that contained 1 mmol/L of dye 8 and 19 mmol/L of 6-[1-O-α-D-mannopyranosyl)-hexanoic acid N-(3-oxa-1H,1H,2H,2H,4H,4H,5H,5H-perfluorotridecyl)-amide was administered interstitially in a skin fold between the toes of the right rear extremity. Five hours after administration, the test animal was sacrificed and opened abdominally. Based on the fluorescence image, the lymph nodes can be localized in situ and the lymph tracts can be visualized. The identification of the lymph nodes in situ is also visually possible by a green coloring, which is caused after interstitial administration of the formulation. The fluorescence of the substances was stimulated by irradiation of the abdominally-opened animal with near-infrared light of wavelength 740 nm, which was produced with an Nd:YAG laser. The fluorescence radiation was detected at a wavelength of >800 nm by an intensified CCD-camera, and the fluorescence images were stored digitally.

Figure 5:
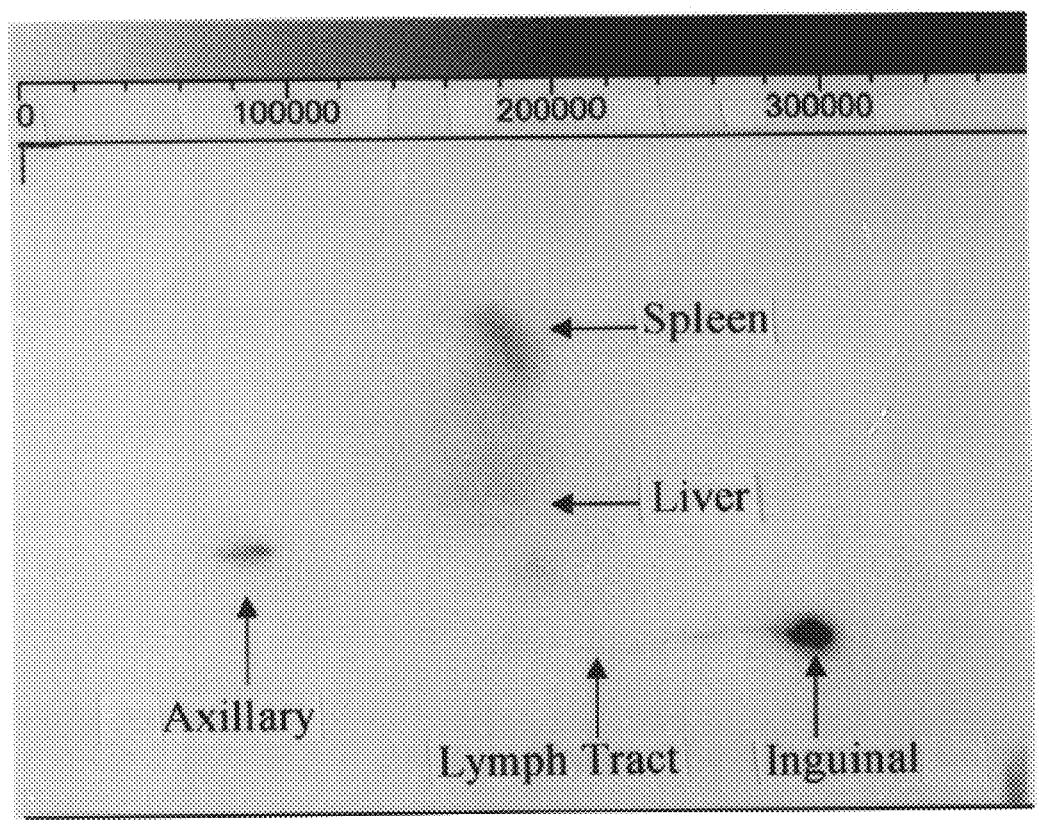
FIG. 5 shows a fluorescence image of an abdominally-opened rat five hours after interstitial administration of a formulation, see Example 21.

FIG. 5 shows a fluorescence image of an abdominally-opened rat five hours after interstitial administration of a formulation with 5 mol % of dye 8 and 95 mol % of mannose in a skin fold between the toes of the right rear extremity. The axillary and the inguinal lymph nodes and a connected lymph tract are visualized based on a fluorescence signal.

EXAMPLE 23

Fluorescence Coloring of Lymph Nodes After Interstitial Administration of a Formulation with 5 mol % of Dye 8 and 95 mol % of 6-[1-O-α-D-Mannopyranosyl)-hexanoic Acid N-(3-oxa-1H,1H, 2H,2H,4H,4H,5H,5H-perfluorotridecyl)-amide From the substance, 0.1 ml of a solution that contained 1 mmol/L of dye 8 and 19 mmol/L of 6-[1-O-α-D-mannopyranosyl]-hexanoic acid N-(3-oxa-1H,1H,2H,2H, 4H,4H,5H,5H-perfluorotridecyl)-amide was administered interstitially in a skin fold between the toes of the right rear extremity of the animal. Five hours after administration, the lymph nodes of the right and left sides of the body were prepared, and a fluorescence image was recorded. The fluorescence of the substances was stimulated by irradiation of the lymph nodes with near-infrared light of wavelength 740 nm, which was produced with an Nd:YAG laser. The fluorescence radiation was detected at a wavelength of >800 nm by an intensified CCD-camera, and the fluorescence images were stored digitally.

Figure 6A:
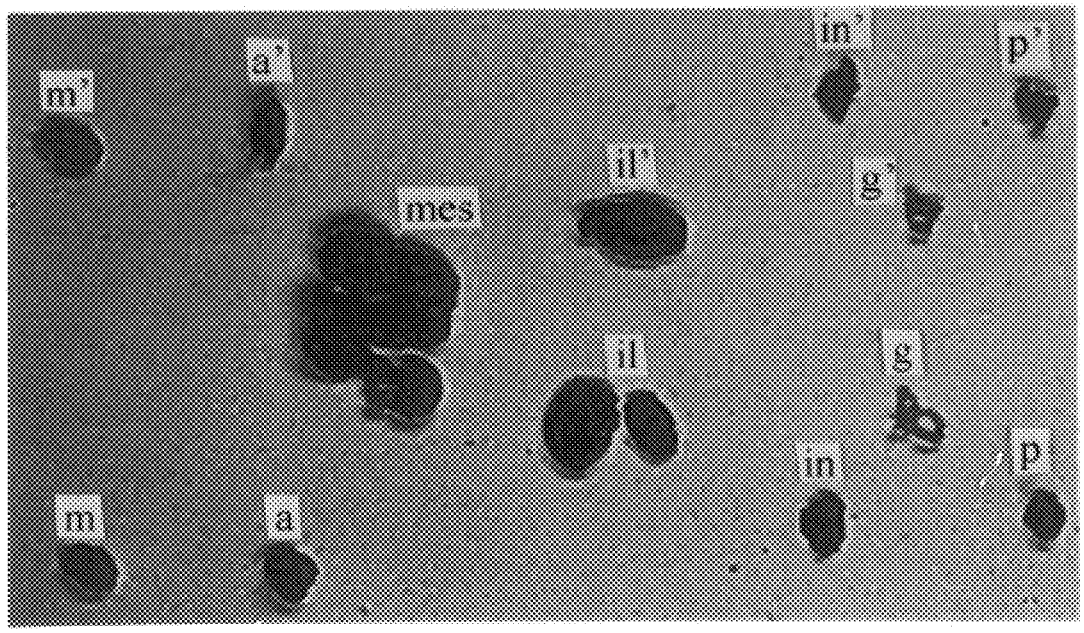
FIG. 6 shows a fluorescence images, (6a) and (6b), of lymph nodes five hours after interstitial administration of a formulation, see Example 23.
Figure 6B:
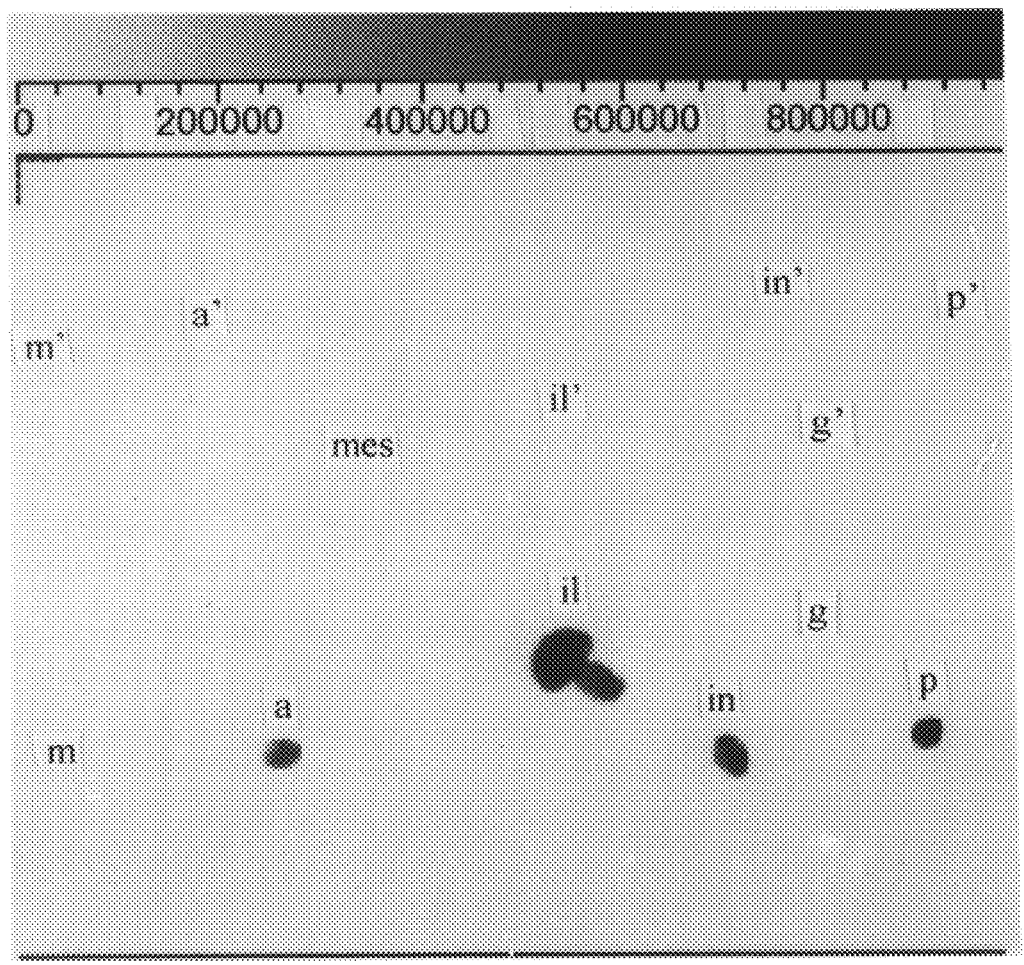

FIG. 6 shows a fluorescence image of lymph nodes five hours after interstitial administration of a formulation with 5 mol % of dye 8 and 95 mol % of 6-[1-O-α-D-mannopyranosyl)-hexanoic acid N-(3-oxa-1H,1H,2H,2H, 4H,4H,5H,5H-perfluorotridecyl)-amide. Shown are the mandibular (m, m'), axillary (a, a'), mesenteric (mes), iliac (il, il'), inguinal (in, in'), gluteal (g, g') and popliteal (p, p') lymph nodes of the animal. Most lymph nodes of the right (administered) side of the body showed a fluorescence signal, while no lymph nodes of the left side of the body (in each case identified with ') had a fluorescence signal. The fluorescence-labeled lymph nodes were greenish-colored because of the accumulation of substances.

Without further elaboration, it is believed that one skilled in the art can, using the preceding description, utilize the present invention to its fullest extent. The above preferred specific embodiments are, therefore, to be construed as merely illustrative, and not limitative of the remainder of the disclosure in any way whatsoever.

In the foregoing and in the above examples, all temperatures are set forth uncorrected in degrees Celsius; and, unless otherwise indicated, all parts and percentages are by weight.

The entire disclosures of all applications, patents and publications, cited above, and of corresponding German application No. 199 48 650.6–43, filed Sep. 29, 1999, and U.S. Provisional Application Serial No. 60/158,306, filed Oct. 8, 1999, are hereby incorporated by reference.

The preceding examples can be repeated with similar success by substituting the generically or specifically described reactants and/or operating conditions of this invention for those used in the preceding examples.

What is claimed is:
1. A compound of formula I

wherein $R_f$ is a straight-chain or branched perfluoroalkyl radical having 4 to 30 carbon atoms, L is a linker and A is a dye molecule according to formula II,

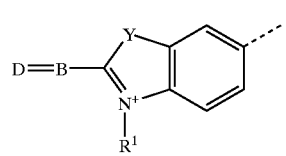

wherein

D is a group of formula III, IV, V or VI, wherein the star denotes the linkage point with B,

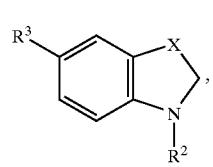

-continued

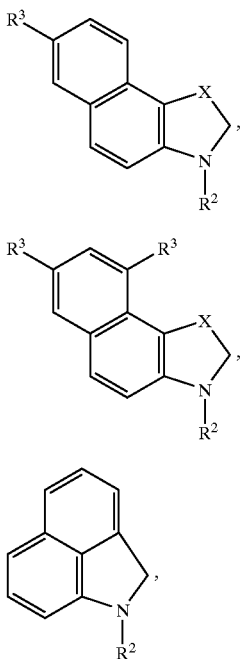

B is a group of formula VII, VIII, IX, X, XI or XII,

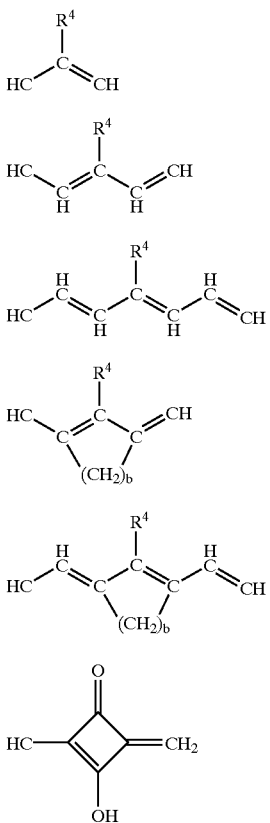

wherein
R$^1$ and R$^2$ are, each independently, a C$_1$–C$_4$ sulfoalkyl chain, or a saturated or unsaturated, branched or straight-chain C$_1$–C$_{50}$ alkyl chain, wherein the alkyl chain or one or more parts of this chain optionally forms one or more aromatic or saturated, cyclic C$_5$–C$_6$ units or bicyclic C$_{10}$ units, and wherein the C$_1$–C$_{50}$ alkyl chain optionally comprises 0 to 15 —O— groups and/or 0 to 3 carbonyl groups and is optionally substituted with 0 to 5 hydroxy groups, R$^3$ is a —COOE$^1$, CONE$^1$E$^2$, —NHCOE$^1$, —NHCONHE$^1$, —NE$^1$E$^2$, —OE$^1$, —OSO$_3$E$^1$, —SO$_3$E$^1$, —SO$_2$NHE$^1$ or —E$^1$ radical, E$^1$ and E$^2$ are, independently of one another, a hydrogen atom, a C$_1$–C$_4$ sulfoalkyl chain, or a saturated or unsaturated, branched or straight-chain C$_1$–C$_{50}$ alkyl chain, wherein the alkyl chain or one or more parts of this chain optionally forms one or more aromatic or saturated cyclic C$_5$–C$_6$ units or bicyclic C$_{10}$ units, and wherein the C$_1$–C$_{50}$ alkyl chain optionally comprises 0 to 15 —O— groups and/or 0 to 3 carbonyl groups, and is optionally substituted with 0 to 5 hydroxy groups, R$^4$ is a hydrogen fluorine, chlorine, bromine or iodine atom, or a branched or straight-chain C$_1$–C$_{10}$ alkyl chain, b is 2 or 3, and X and Y are, independently of one another, —CH═CH— or C(CH$_3$)$_2$.

2. A compound according to claim 1, wherein L is a direct bond or a straight-chain or branched carbon chain having up to 20 carbon atoms, which is optionally substituted with one or more —OH, —COOH, —SO$_3$ groups and optionally comprises one or more —O—, —S—, —CO—, —CONH—, —NHCO—, —CONR—, —NRCO—, —SO$_2$—, —NH—, —NR groups or a piperazine as part of the carbon chain, wherein R is a C$_1$ to C$_{10}$ alkyl radical, which is optionally substituted with one or more OH groups.

3. A galenical formulation, comprising
a) at least one perfluoroalkyl-containing dye molecule of Formula I,

 (I)

wherein
R$_f$ is a straight-chain or branched perfluoroalkyl radical having 4 to 30 carbon atoms,
L is a linker, and
A is a dye molecule of Formula II,

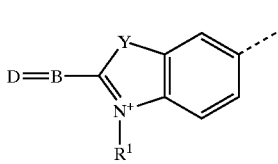 II wherein
D is a group of formula III, VI, V or VI, wherein the star denotes the linkage point with B,

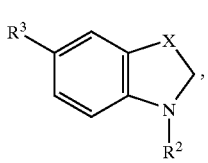 III

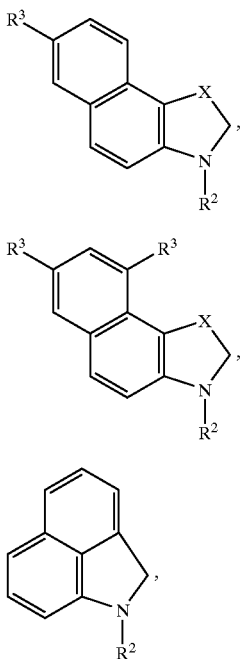

B is a group of formula VII, VIII, IX, X, XI or XII,

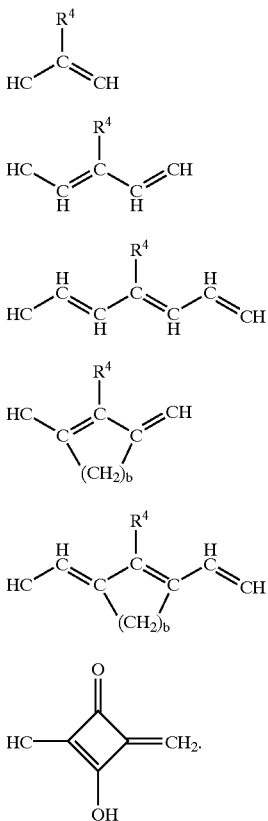

R$^1$ and R$^2$ are, each independently, a C$_1$–C$_4$ sulfoalkyl chain, or a saturated or unsaturated, branched or straight-chain C$_1$–C$_{50}$ alkyl chain, wherein the alkyl chain or one or more parts of said chain optionally forms one or more aromatic or saturated, cyclic C$_{5-C6}$ units or bicyclic C$_{10}$ units, and wherein the C$_1$–C$_{50}$ alkyl chain optionally comprises 0 to 15 —O— groups and or 0 to 3 carbonyl groups and is optionally substituted with 0 to 5 hydroxy groups, R$^3$ is a —COOE$^1$, —CONE$^1$E$^2$, —NHCOE$^1$, —NHCONHE$^1$, —NE$^1$E$^2$, —OE$^1$, —OSO$_3$E$^1$, —SO$_3$E$^1$, —SO$_2$NHE$^1$ or —E$^1$ radical, E$^1$ and E$^2$ are, independently of one another, a hydrogen atom, a C$_1$–C$_4$ sulfoalkyl chain, or a saturated or unsaturated, branched or straight-chain C$_1$–C$_{50}$ alkyl chain, wherein the alkyl chain or one or more parts of said chain optionally forms one or more aromatic or saturated cyclic C$_5$–C$_6$ units or bicyclic C$_{10}$ units, and wherein the C$_1$–C$_{50}$ alkyl chain optionally comprises 0 to 15 —O— groups and/or 0 to 3 carbonyl groups, and is optionally substituted with 0 to 5 hydroxy groups, R$^4$ is a hydrogen, fluorine, chlorine, bromine or iodine atom, or a branched or straight-chain C$_1$–C$_{10}$ alkyl chain, b is 2 or 3, and X and Y are, independently of one another, —CH=CH— or C(CH$_3$)$_2$, and b) at least one perfluoroalkyl-containing metal complex.

4. A formulation according to claim 3, wherein the at least one perfluoroalkyl-containing dye molecule of Formula I and the at least one perfluoroalkyl-containing metal complex are dissolved in a solvent forming a solution.

5. A formulation according to claim 4, wherein the solvent is water.

6. A formulation according to claim 4, wherein the at least one perfluoroalkyl-containing dye mole % of Formula I comprises 1 to 10 molecule of the total moles of the at least one perfluoroalkyl-containing dye molecule of formula I and the at least one perfluoroalkyl-containing metal complex in the solution.

7. A formulation according to claim 5, wherein the at least one perfluoroalkyl-containing dye molecule of formula I absorbs and fluoresces in a spectral range of 400 to 900 nm.

8. A formulation according to claim 3, wherein L is a direct bond or a straight-chain or branched carbon chain having up to 20 carbon atoms, which is optionally substituted with one or more —OH, —COOH, —SO$_3$ groups and/or optionally comprises one or more —O—, —S—, —CO—, —CONH—, —NHCO—, —CONR—, —NRCO—, —SO$_2$—, —NH—, —NR— groups or a piperazine as part of the carbon chain, wherein R is a C$_1$ to C$_{10}$ alkyl radical, which is optionally substituted with one or more OH groups and optionally comprises one or more —O— groups, as part of the alkyl radical.

9. A formulation according to claim 3, wherein the at least one perfluoroalkyl-containing metal complex is the gadolinium complex of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane, the gadolinium complex of 10-[2-hydroxy-4-aza-5-oxo-7-oxa-10,10,11,11,12,12,13,13,14,14,15,15,16,16,17,17,17-heptadecafluoroheptadecyl]-1,4,7tris(carboxymethyl)-1,4,7,10-tetraazacyclododecane, 1,4,7-tris {1,4,7-tris(N-carboxylatomethyl)-10(N-1-methyl-3,6-diaza-2,5,8-trioxooctane-1,8-diyl)-1,4,7,10-tetraazacyclododecane, Gd-complex}-10-(N-2H,2H,4H,4H,5H,5H-3-oxa-perfluoro-tridecanoyl)- 1,4,7,10-tetraazacyclododecane, 1,4,7-tris{1,4,7-tris[(N-carboxylatomethyl)]-10-[N-1-methyl-3-aza-2,5-dioxopentam-1,5-diyl]-1,4,7,10-tetrazacyclododecane, Gd complex}-10-[2-N-ethyl-N-perfluorooctylsulfonyl)-amino]-acetyl-1,4,7,10-tetraazacyclododecane, the gadolinium complex of 10-[2-hydroxy-4-aza-5oxo-7-aza-7 (perfluoroctylsulfonyl)-nonyl]-1,4,7-tris(carboxymethyl)-1,4,7,10-tetraazacyclododecane, 1,4,7-tris(carboxylatomethyl)-10-[(3-aza-4-oxo-hexan-5-ylic)-acid-N-(2,3-dihydroxy-propyl)-N(1H,1H,2H,2H,4H,4H,5H,5H-3-oxa)-perfluorotridecyl)-amide]1,4,7,10-tetraazacyclododecane, gadolinium complex, 1,4,7-tris(carboxylatomethyl)-10-[(3-aza4-oxo-hexan-5-ylic)-acid-N-(1H,1H,2H,2H,4H,4H,5H,5H-3-oxa-perfluorotridecyl)-amide]-1,4,7,10-tetraazacyclododecane, gadolinium complex, 1,4,7-tris(carboxylatomethyl)-10-{(3-aza-4-oxo-hexan-5-ylic)-acid-[N-3,6,9,12,15-pentaoxa)-hexadexyl)-N-(1H,1H,2H,2H,4H,4H,5H,5H-3-oxa)-perfluorotridecyl)]-amide}-1,4,7,10-tetraazacyclododecane, gadolinium complex, or 1,4,7-tris(carboxylatomethyl)-10-[(3-aza-4-oxo-hexan-5-ylic)-acid-N-[(5-hydroxy-3-oxa-pentyl)-N-(1H,1H,2H,2H,4H,4H,5H,5H-3-oxa)-perfluorotridecyl)-amide]-1,4,7,10-tetraazacyclododecane, gadolinium complex.

10. A formulation according to claim 3, wherein the at least one perfluoroalkyl-containing dye molecule of Formula I and the at least one perfluoroalkyl-containing metal complex each comprise a perfluoroalkyl chain having 6 to 12 carbon atoms.

11. A formulation according to claim 3, wherein the at least one perfluoroalkyl-containing dye molecule of Formula I and the at least one perfluoroalkyl-containing metal complex each comprise a perfluoroalkyl chain having 8 carbon atoms.

12. A process for the preparation of a galenical formulation according to claim 3, wherein the at least one perfluoroalkyl-containing dye molecule of Formula I and the at least one perfluoroalkyl-containing metal complex are dissolved in a solvent while stirred vigorously.

13. A process for the preparation of a galenical formulation according to claim 3, wherein the at least one perfluoroalkyl-containing dye molecule of Formula I and the at least one perfluoroalkyl-containing metal complex are dissolved in a solvent while treated with ultrasound.

14. A process for the preparation of a galenical formulation according to claim 3, wherein the at least one perfluoroalkyl-containing dye molecule of Formula I and the at least one perfluoroalkyl-containing metal complex are dissolved in a solvent while treated with a microwave.

15. A process for the preparation of a galenical formulation according to claim 3, wherein the at least one perfluoroalkyl-containing dye molecule of Formula I is dissolved in a solvent forming a solution, the at least one perfluoroalkyl-containing metal complex is dissolved in another solvent forming a solution, the two solutions are combined, and one of the two solvents is distilled off.

16. A formulation according to claim 4, which is solid.

17. A process for the preparation of a formulation according to claim 16, wherein the solution is freeze-dried.

18. A method for optical diagnosis, fluorescence diagnosis, near-infrared diagnosis, nuclear spin tomography or ultrasound imaging, comprising administering a formulation of claim 3 as a contrast medium.

19. A method for visualizing lymph nodes or blood pools, comprising administering a formulation of claim 3 as a contrast medium.

20. A method for intraoperative diagnosis, comprising administering a formulation of claim 3 as a contrast medium.

* * * * *

UNITED STATES PATENT AND TRADEMARK OFFICE
CERTIFICATE OF CORRECTION

PATENT NO. : 6,447,749 B1
DATED : September 10, 2002
INVENTOR(S) : Licha et al.

It is certified that error appears in the above-identified patent and that said Letters Patent is hereby corrected as shown below:

Column 38,
Line 2, reads "$c_6$" should read -- $C_6$ --
Line 34, reads "dye mole %" should read -- dye molecule --
Line 35, reads "molecule" should read -- mol % --
Line 39, reads "claim 5" should read -- claim 3 --

Column 39,
Line 3, reads "tetrazacyclododecane" should read -- tetraazacyclododecane --

Signed and Sealed this

Twenty-eighth Day of September, 2004

JON W. DUDAS
*Director of the United States Patent and Trademark Office*